US006235777B1

(12) United States Patent
Ohuchida et al.

(10) Patent No.: US 6,235,777 B1
(45) Date of Patent: May 22, 2001

(54) BENZENESULFONAMIDE COMPOUNDS

(75) Inventors: Shuichi Ohuchida; Yuuki Nagao; Takayuki Maruyama, all of Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/078,577

(22) Filed: May 14, 1998

(30) Foreign Application Priority Data

May 15, 1997 (JP) .................................................. 9-140959

(51) Int. Cl.[7] .................................................. A61K 31/21

(52) U.S. Cl. .......................... 514/510; 514/538; 514/562; 514/618; 560/12; 562/427; 562/430; 564/90

(58) Field of Search .............................. 560/12; 562/427, 562/430; 564/90; 514/510, 538, 562, 618

(56) References Cited

U.S. PATENT DOCUMENTS

| | | |
|---|---|---|
| 4,861,913 | 8/1989 | Narisada et al. . |
| 5,168,101 | 12/1992 | Arai et al. . |
| 5,663,417 | 9/1997 | Hamanaka et al. . |

*Primary Examiner*—Samuel Barts
(74) *Attorney, Agent, or Firm*—Stevens, Davis, Miller & Mosher, L.L.P.

(57) ABSTRACT

A benzenesulfonamide compound of the formula (I)

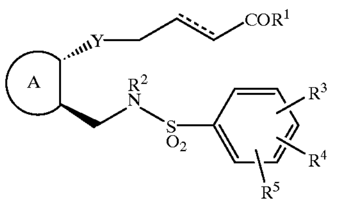

(I)

($R^1$ is hydroxy, C1~4 alkoxy, $NR^6R^7$ (each $R^6$ and $R^7$ is, independently, H or C1~4 alkyl.); $R^2$ is H, C1~4 alkyl; $R^3$, $R^4$ are C1~4 alkyl, halogen trifluoromethyl; $R^5$ is H, C1~4 alkyl, halogen, trifluoromethyl; Y is cis-vinylene, trans-vinylene; and the symbol (i)

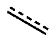

(i)

is single bond, double bond.), non-toxic salt thereof or cyclodextrin clathrate thereof and an antagonist of EP1 receptor which is a prostaglandin $E_2$ receptor subtype comprising it as an active ingredient.

The present invention compounds of the of the formula (I) can bind strongly to EP1 receptor which is a prostaglandin $E_2$ receptor subtype and scarcely bind to the other receptor subtypes. Therefore, they are considered to be useful as antipyretic agents, as analgesics or as treating agent for pollakiuria having little side effect.

20 Claims, No Drawings

BENZENESULFONAMIDE COMPOUNDS

SUMMARY

The present invention relates to the benzenesulfonamide compounds. More detailed, the present invention relates to (1) the compounds of the formula (I):

(I)

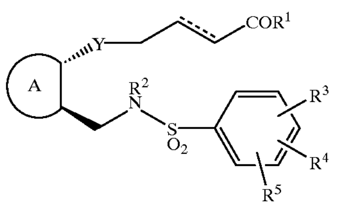

wherein, all symbols are the same meaning as defined hereinafter, (2) the process for the preparation of them and (3) Prostaglandin $E_2$ receptor antagonists which comprise them as an active ingredient.

BACKGROUND

Prostaglandin $E_2$ (abbreviated as $PGE_2$) has been known as metabolite in the arachidonate cascade. It has been known that $PGE_2$ possesses cyto-protective activity, uterine contraction, induce of pain, promotion of digestive peristalsis, awakening effect, suppression of gastric acid secretion or reduction of blood pressure and diuretic activity etc.

In the recent study, it was found that $PGE_2$ receptor was divided into some subtypes which possess different physical role from each other. At present, four receptor subtypes are known and they are called EP1, EP2, EP3 and EP4 (Negishi M. et al, J. Lipid Mediators Cell Signalling 12, 379–391 (1995)).

$PGE_2$ possesses a variety of physiological activities, so the undesired action other than the aimed one is shown as side effect. The research for the role of each receptor subtype and the investigation of the compound which only shows the effect on the specific subtype have been carried out to overcome such a problem.

In these subtypes, it has been known that EP1 subtype relates to induce of pain, fever and diuresis (Br. J. Pharmacol. 1994, 112, 735–40; European J. Pharmacol. 152 (1988) 273–279; Gen Pharmacol. September 1992, 23(5) p805–809). Therefore, to antagonize against this receptor is considered to be useful as analgesics, as antipyretic agent and as treating agent for pollakiuria.

The present inventors et. al. have studied to find the compound which can bind to EP1 receptor selectively, have found that the benzenesulfonamide compounds of the formula (I) can bind to EP1 receptor selectively and strongly and scarcely bind to other receptor subtypes, and then have achieved the present invention.

RELATED ARTS

As for the compound having a similar structure of the present invention compound of the formula (I), the following related arts have been known.

In the specification of Japanese Patent Application Kokai Hei 6-279395 (U.S. Pat. No. 5,663,417 or European Patent Publication No. 608,847), it was disclosed that the sulfonamide compound possessing carbocyclic ring of the formula (A)

(A)

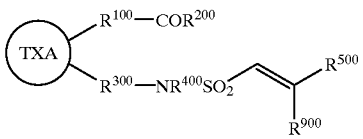

wherein, the symbol

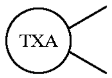

is (i) the group of the formula

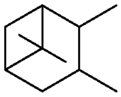 , 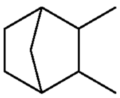 , 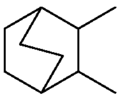 ,

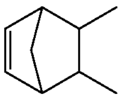 , 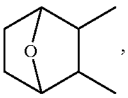 , 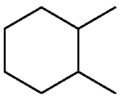 or

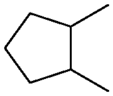

or (ii) the group of the formula

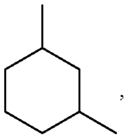 , 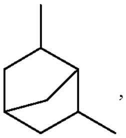 , 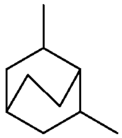 or

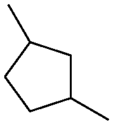

$R^{100}$ is C4–7 alkylene or C4–7 alkenylene, $R^{200}$ is hydroxy, C1~20 alkoxy or $NR^{230}R^{240}$ in which each $R^{230}$ and $R^{240}$ is, independently, hydrogen, C1~4 alkyl or $NR^{230}R^{240}$ is amino acid residue, $R^{300}$ is single bond or C1~4 alkylene, $R^{400}$ is hydrogen or C1~4 alkyl, each $R^{500}$ and $R^{900}$ is, independently, (i)

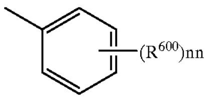

wherein, $R^{600}$ is hydrogen, C1~4 alkyl, C1~4 alkoxy, hydroxy, halogen, trifluoromethyl or nitro, and nn is 1, 2 or 3, (ii)

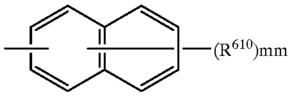

wherein, $R^{610}$ is hydrogen, C1~4 alkyl, C1~4 alkoxy, hydroxy, halogen, trifluoromethyl or nitro, and mm is 1, 2 or 3, (iii)

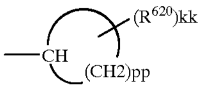

wherein, $R^{620}$ is hydrogen, C1~4 alkyl, C1~4 alkoxy, hydroxy, halogen, trifluoromethyl or nitro, and kk is 1, 2 or 3, (iv) C1~7 alkyl or (v) hydrogen, cyclodextrin clathrate thereof and non-toxic salt thereof, and the compound of the formula (B)

(B)

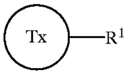

wherein, $R^1$ is i) $COOR^{11}$, or ii) $CONR^{13}R^{14}$ in which $R^{11}$ is hydrogen, C1~20 alkyl, and each $R^{13}$ and $R^{14}$ is hydrogen, C1~4 alkyl, or $NR^{13}R^{14}$ is amino acid residue, and the symbol

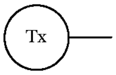

is (Aa)

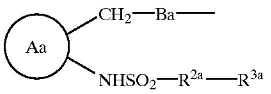

(Ab)

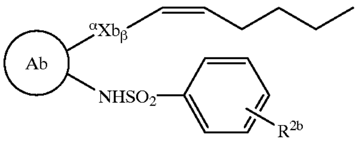

or (Ac)

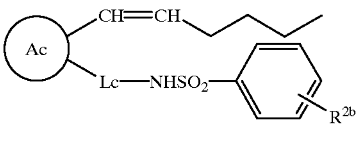

wherein, the symbol

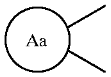

is the group of the formula (Aa-1)

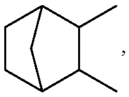

, (Aa-2)

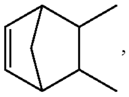

, (Aa-3)

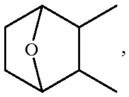

, (Aa-4)

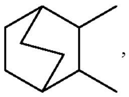

, (Aa-5)

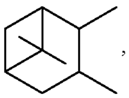

, (Aa-6)

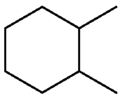

or (Aa-7)

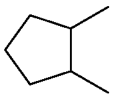

Ba is i)—$CH_2$—$CH_2$—$(CH_2)_m$— or ii) cis-CH═CH—$(CH_2)_m$— in which m is 1~6, $R^{2a}$ is single bond or C1~4 alkylene, $R^{3a}$ is benzene, naphthalene or C4–7 cycloalkyl unsubstituted or substituted by 1 to 3 of C1~4 alkyl, C1~4 alkoxy, hydroxy, cyano, halogen, trifluoromethyl or nitro, or $R^{2a}$ and $R^{3a}$ together forms C1~12 alkyl, the symbol

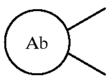

is the group of the formula (Ab-1)

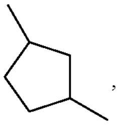

, (Ab-2)

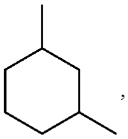

, (Ab-3)

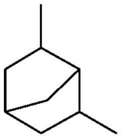

or (Ab-4)

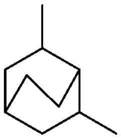

Xb is i) single bond, ii) C1~4 alkylene or iii) C2~4 alkenylene, with the proviso that group of -αCH═CH—$CH_2$β- and -α$CH_2$—CH═CH—$CH_2$β- is excluded, $R^{2b}$ is hydrogen, C1~4 alkyl, C1~4 alkoxy, hydroxy, cyano, halogen, trifluoromethyl or nitro, configuration of C5–C6 double bond in the formula (Ab) is cis, the symbol

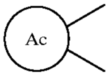

is the group of the formula (Ac-1)

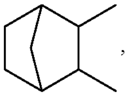

, (Ac-2)

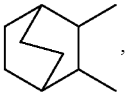

, (Ac-3)

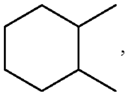

,

-continued (Ac-4)

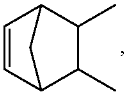

, (Ac-5)

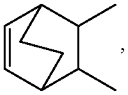

, (Ac-6)

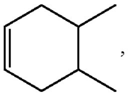

, (Ac-7)

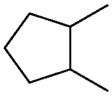

or (Ac-8)

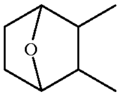

Lc is C1~4 alkylene, $R^{2c}$ is hydrogen, C1~4 alkyl, C1~4 alkoxy, hydroxy, cyano, halogen, trifluoromethyl or nitro, and the configuration of C5–C6 bond in the formula (Ac) is cis or trans, cyclodextrin clathrate thereof and non-toxic salt thereof are useful for the prevention and/or treatment of abortifacient, pain, diarrhea or sleeping disorder as $PGE_2$ receptor antagonist or for the prevention and/or treatment of constipation, ulcer, gastritis and hypertension, or induction of labor as $PGE_2$ agonist.

On the other hand, there are the following two patent applications relate to similar structure compound showing the different activity.

That is to say, in Japanese patent application Kokai Hei 2-180862 (U.S. Pat. No. 5,168,101 or European Patent Publication No. 312,906) and Japanese patent application Kokai Sho 63-139161 (U.S. Pat. No. 4,861,913 or European Patent Publication No. 226,346), it was disclosed that the compounds having a similar structure of the present invention compounds showed Thromboxane A2 antagonistic activity.

DISCLOSURE OF THE INVENTION

The present invention relates to (1) the benzenesulfonamide compounds of the formula (I)

(I)

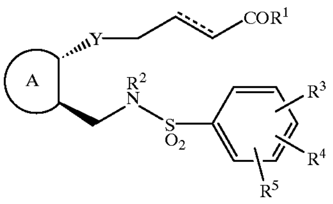

wherein, the formula

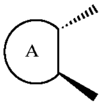

is the group of the formula (a)

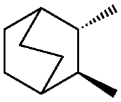

, (b)

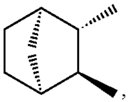

, (c)

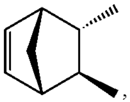

, (d)

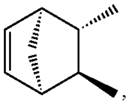

, (e)

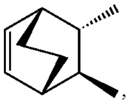

, (f)

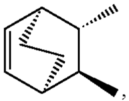

, (g)

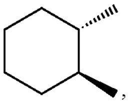

, (h)

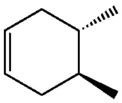

or (i)

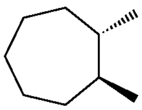

$R^1$ is hydroxy, C1~4 alkoxy or the group of the formula $NR^6R^7$ in which each $R^6$ and $R^7$ is, independently, hydrogen or C1~4 alkyl, $R^2$ is hydrogen or C1~4 alkyl, $R^3$ and $R^4$ are C1~4 alkyl, halogen or trifluoromethyl, $R^5$ is hydrogen, C1~4 alkyl, halogen or trifluoromethyl, Y is cis-vinylene or trans-vinylene, and the symbol

is single bond or double bond, non-toxic salt thereof or cyclodextrin clathrate thereof, (2) the process for preparation of them and (3) an antagonist of EP1 receptor which is a $PGE_2$ receptor subtype comprising them as an active ingredient.

In the formula (I), C1~4 alkyl represented by $R^2$ to $R^7$ means methyl, ethyl, propyl, butyl and isomer thereof.

In the formula (I), C1~4 alkoxy represented by $R^1$ means methoxy, ethoxy, propoxy, butoxy and isomer thereof.

In the formula (I), halogen represented by $R^3$ to $R^5$ means fluorine, chlorine, bromine and iodine.

Unless otherwise specified, in the present invention, the symbol

indicates that the substituent attached thereto is in front of the sheet and the symbol

indicates that the substituent attached thereto is behind the sheet as clear for the skilled person in the art.

Unless otherwise specified, all isomers are included in the present invention. For example, alkyl includes straight-chain or branched-chain ones. Isomers generated by asymmetric carbon(s) e.g. branched alkyl are also included in the present invention.

In the present invention compounds of the formula (I), the compounds described in the Examples, 5-cis type compounds of the following Tables, the corresponding ester and/or 5-trans type compounds and the corresponding amide and/or 5-trans type compounds are preferable. These ester and amide compounds are preferable as prodrug of the corresponding carboxylic acid compounds.

In the present invention compounds of the formula (I), the compounds of the formula (I-1)

(I-1)

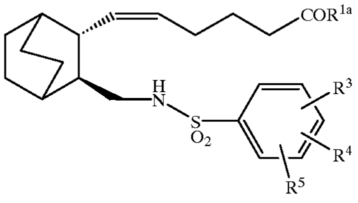

wherein, $R^{1a}$ is hydroxy or C1~4 alkoxy, and the other symbols are the same meaning as defined hereinbefore are also preferable.

(1)
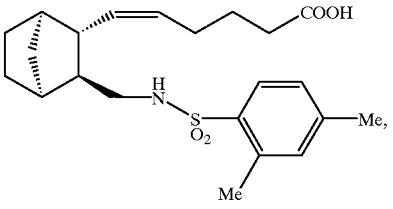
(2)
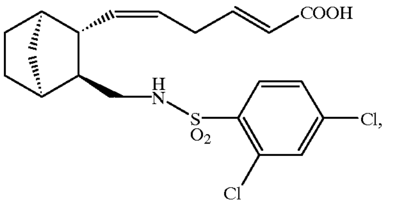
(3)
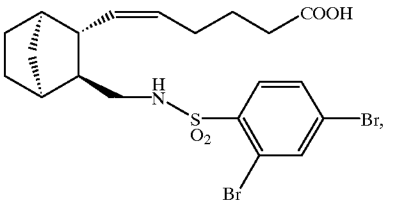
(4)
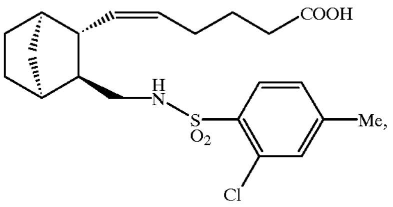
(5)
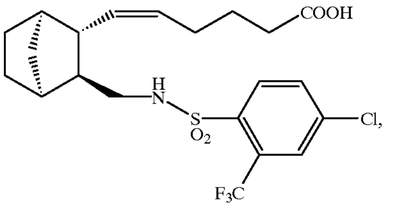
(6)
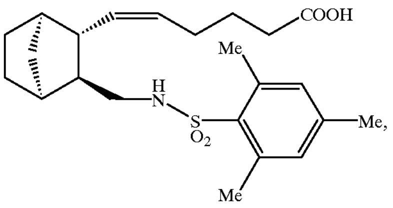
(7)
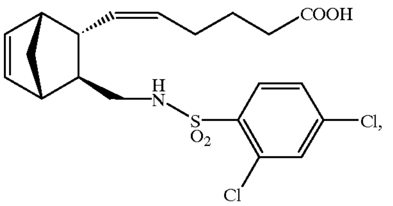
-continued
(8)
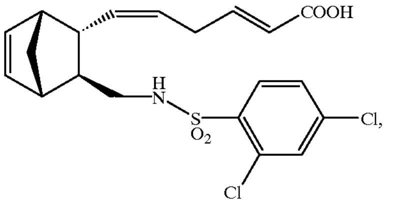
(9)
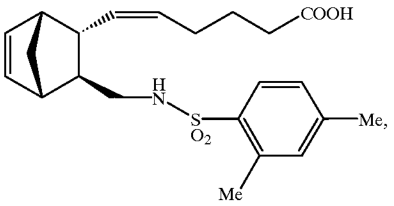
(10)
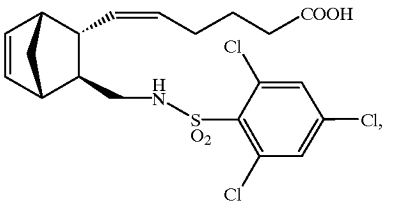
(11)
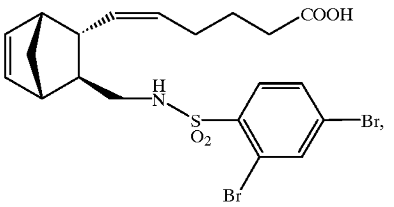
(12)
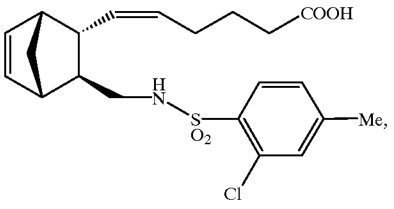
(13)
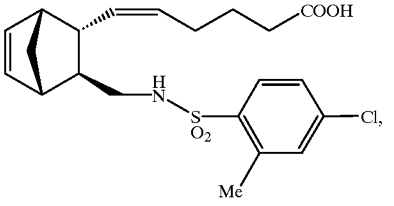
(14)
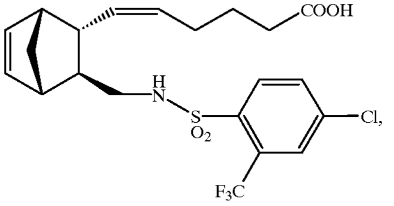

-continued
(15)
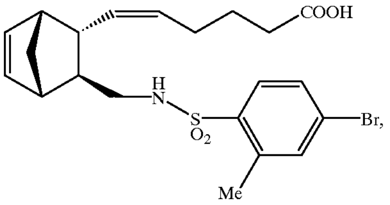
(16)
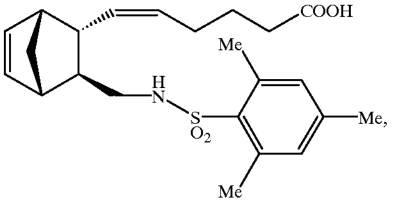
(17)
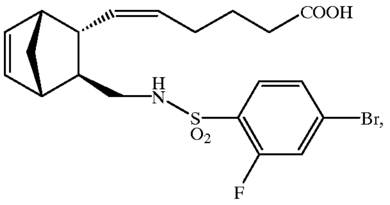
(18)
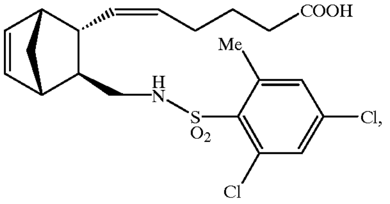
(19)
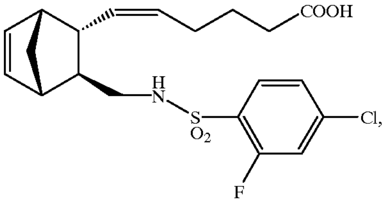
(20)
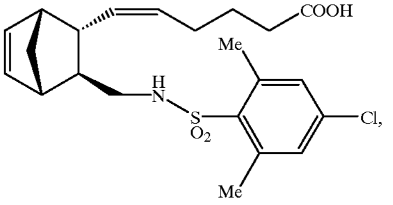
(21)
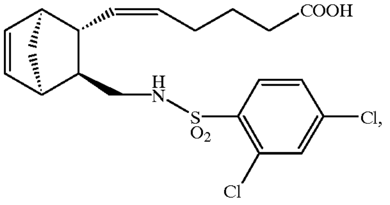
-continued
(22)
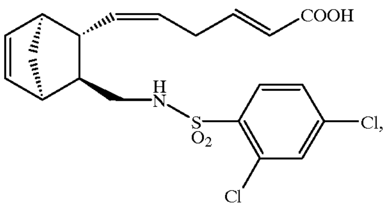
(23)
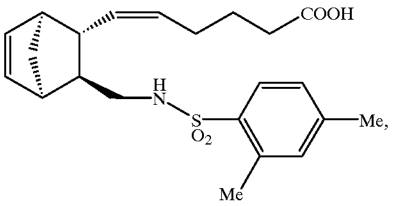
(24)
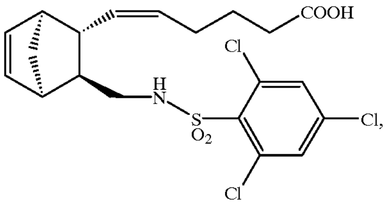
(25)
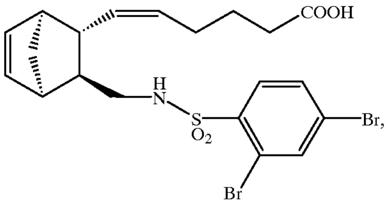
(26)
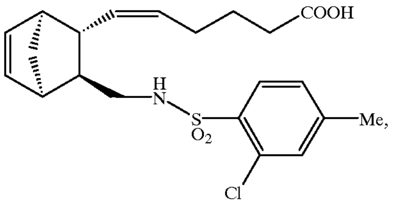
(27)
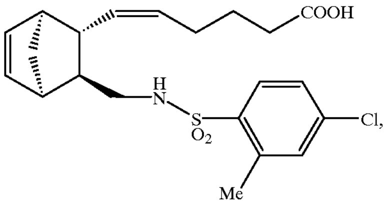
(28)
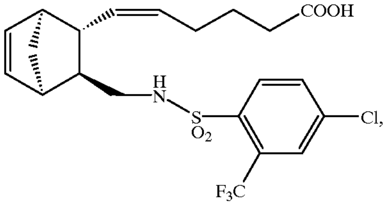

-continued
(29)
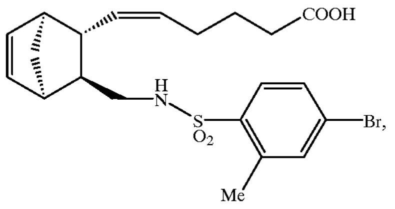
(30)
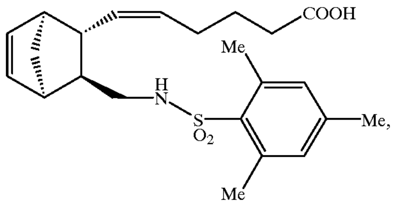
(31)
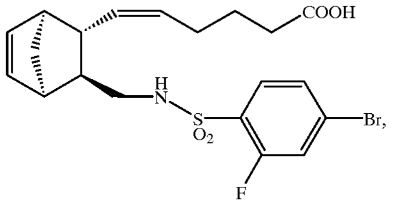
(32)
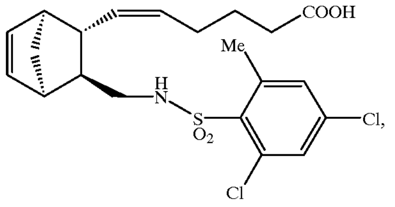
(33)
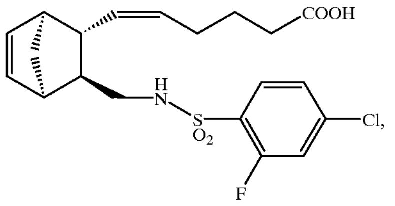
(34)
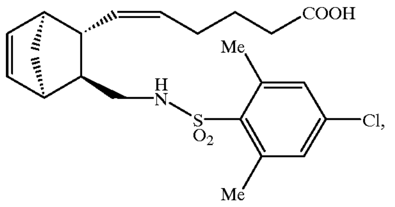
(35)
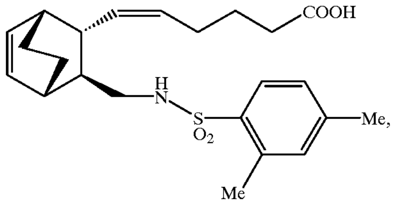
-continued
(36)
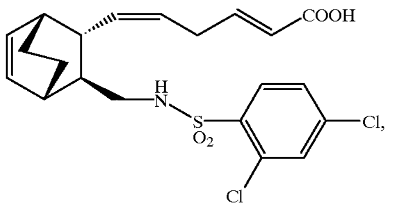
(37)
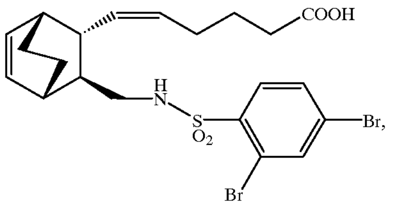
(38)
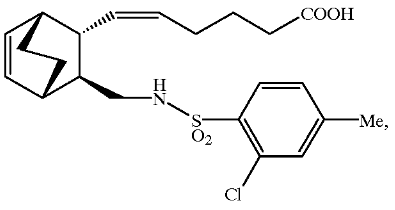
(39)
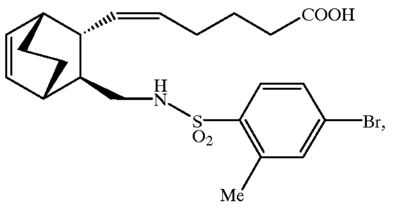
(40)
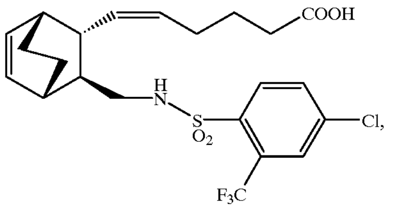
(41)
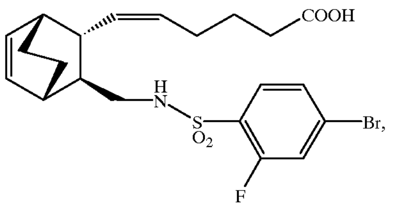
(42)
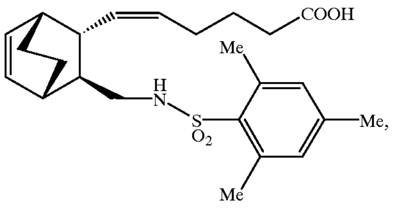

-continued
(43)
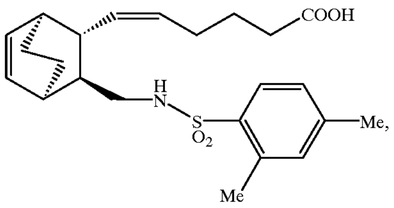
(44)
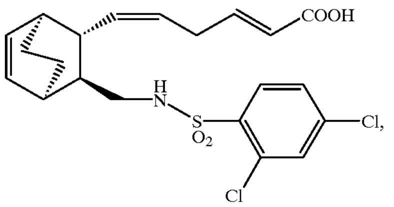
(45)
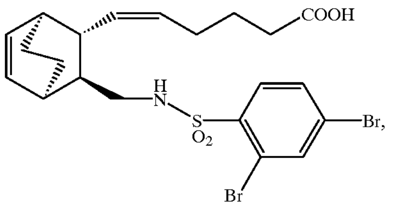
(46)
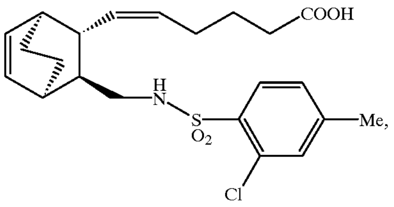
(47)
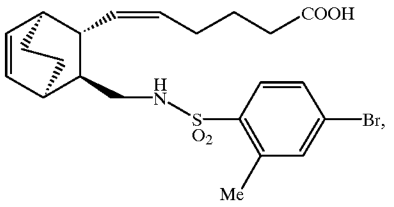
(48)
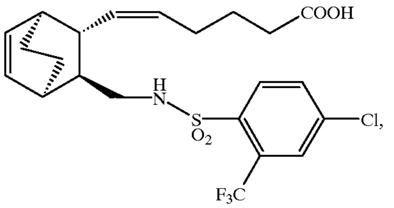
(49)
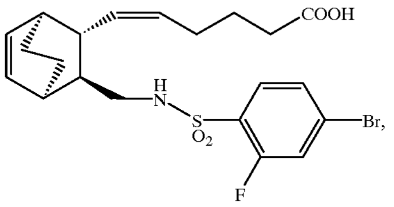
-continued
(50)
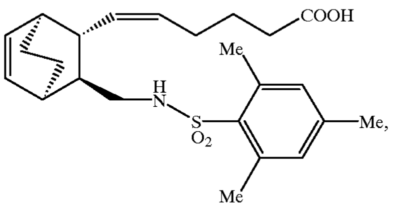
(51)
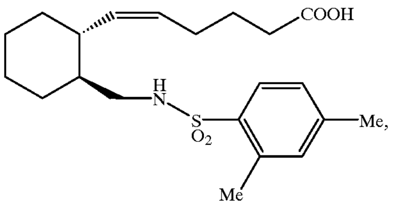
(52)
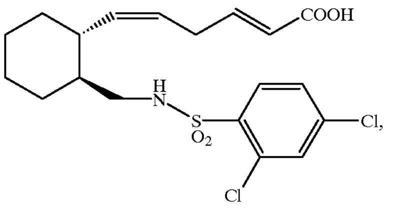
(53)
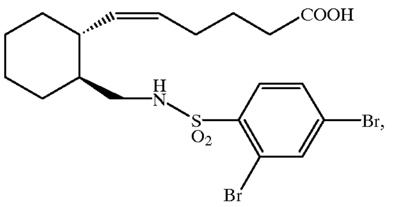
(54)
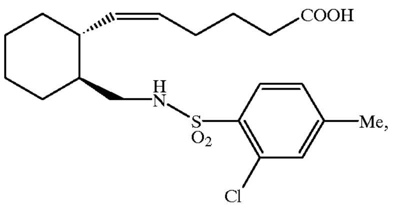
(55)
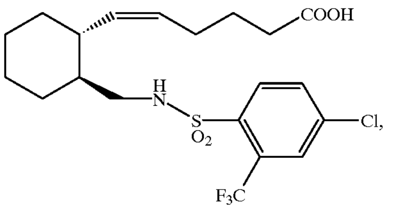
(56)
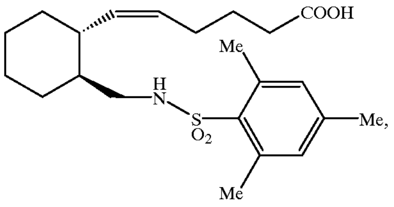

-continued
(57)
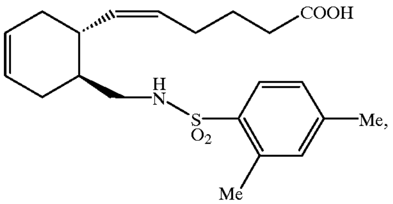
(58)
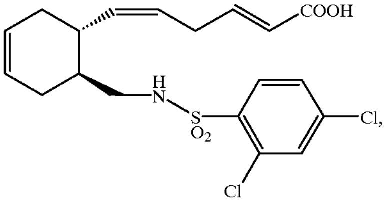
(59)
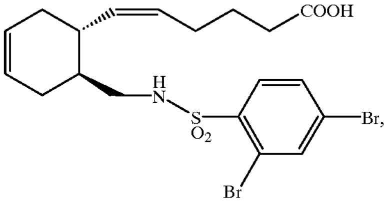
(60)
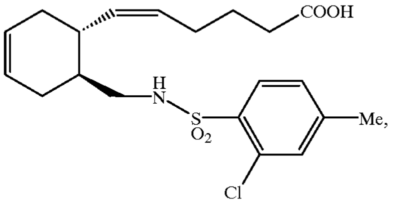
(61)
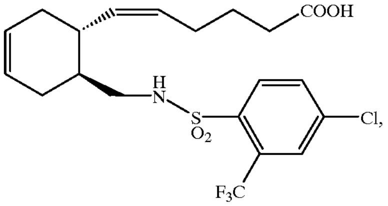
(62)
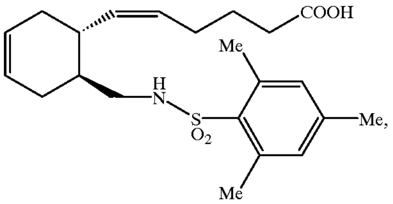
(63)
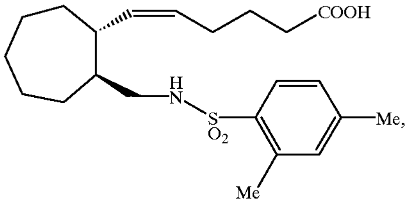
-continued
(64)
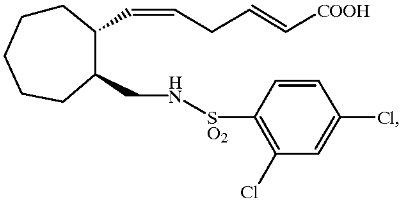
(65)
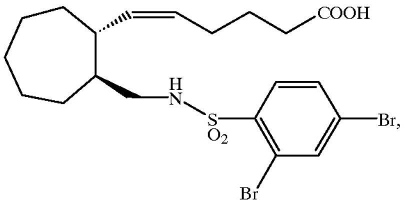
(66)
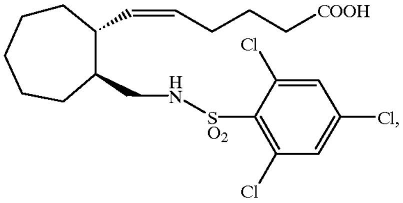
(67)
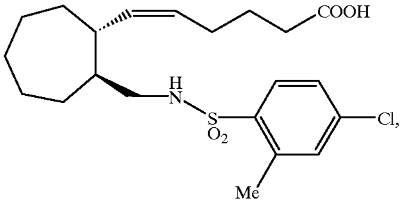
(68)
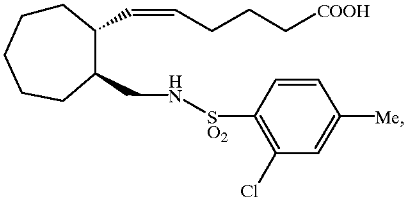
(69)
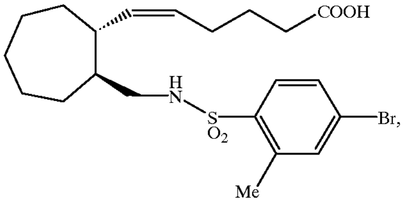
(70)
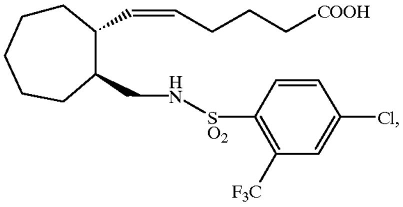

-continued (71)

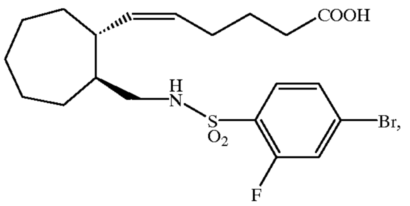

(72)

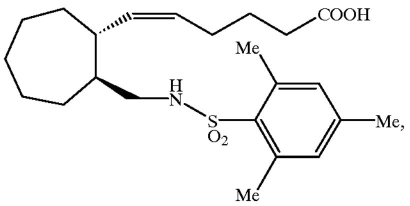

(73)

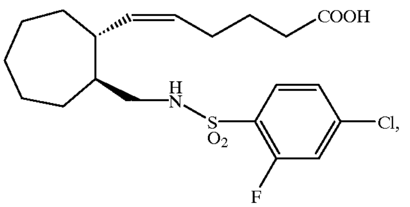

(74)

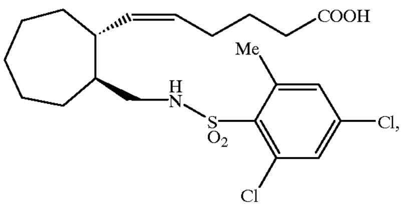

(75)

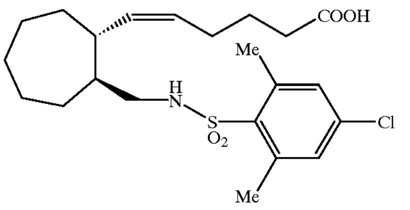

Salts

The compounds of the present invention of the general formula (I) may be converted into the corresponding salts by known methods. Non-toxic and water-soluble salts are preferable. Suitable salts, for example, are as follows: salts of alkaline metals (potassium, sodium etc.), salts of alkaline earth metals (calcium, magnesium etc.), ammonium salts, salts of pharmaceutically acceptable organic amines (tetramethylammonium, triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine etc.).

Cyclodextrin Clathrates

The present invention compounds of the formula (I) may be converted into their cyclodextrine clathrate with using α-, β- or γ-cyclodextrin or mixture thereof by the method described in the specification of Japanese Patent Kokoku Sho 50-3362, 52-31404 or 61-52146. Converting into their cyclodextrin clathrates serves to increase the stability and solubility in water and therefor it is useful in the use for pharmaceuticals.

Process for the Preparation of the Present Invention Compound

The present invention compounds of the formula (I) may be prepared by the following process, the method described in the Examples or the known methods.

(1) In the present invention compounds of the formula (I), a compound wherein $R^1$ is hydroxy or C1~4 alkoxy, i.e., a compound of the formula (Ia)

(Ia)

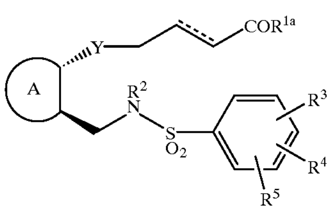

wherein, $R^{1a}$ is hydroxy or C1~4 alkoxy, and the other symbols are the same meaning as defined hereinbefore may be prepared by (a) reacting a compound of the formula (II)

(II)

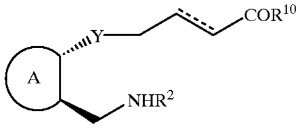

wherein, $R^{10}$ is C1~4 alkoxy, and the other symbols are the same meaning as defined hereinbefore or salt thereof with a compound of the formula (III)

(III)

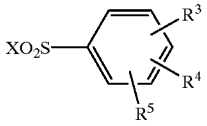

wherein, X is halogen, and the other symbols are the same meaning as defined hereinbefore to form amide bond and, if necessary, followed by hydrolysis under an alkaline condition or with using an enzyme or (b) reacting a compound of the formula (XI)

(XI)

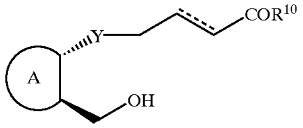

wherein, all symbols are the same meaning as defined hereinbefore with a compound of the formula (III-A)

(III-A)

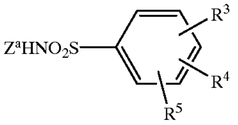

wherein, $Z^a$ is C1~4 alkyl or amino-protecting group which may be removed under an acidic condition, and the other symbols are the same meaning as defined hereinbefore and, if necessary, followed by removing an amino-protecting group under an acidic condition and/or by hydrolysis under an alkaline condition or with using an enzyme.

Reaction to form amide bond is well known. For example, it may be carried out in an organic solvent (methylene chloride, tetrahydrofuran (THF), benzene, acetone or acetonitrile etc.) in the presence or absence of tertiary amine (triethylamine, dimethylaminopyridine or pyridine etc.) by using or without a condensing agent ((1-ethyl-3-[3-(dimethylamino)propyl]carbodiimido (EDC), 1,3-dicyclohexylcarbodiimido (DCC) etc.) at −10~50° C.

The hydrolysis under an alkaline condition is known. For example, it may be carried out in a water-miscible organic solvent (THF, methanol, ethanol, dimethoxyethane or mixture thereof etc.), by using an alkaline (e.g., sodium hydroxide, potassium hydroxide etc.) solution, at 0~50° C.

The hydrolysis with using an enzyme is known. For example, it may be carried out in a mixture solution of water-miscible organic solvent (ethanol, dimethylsulfoxide or mixture thereof etc.) and water, in the presence or absence of buffer, by using esterase (esterase, lipase etc.), at 0~50° C.

The reaction of an alcohol compound of the formula (XI) with an amine compound of the formula (III-A) may be carried out by known methods. For example, it may be carried out in an organic solvent (acetone, THF, methylene chloride), in the presence of triphenylphosphine and diethylazo dicarboxylate at 0~50° C.

Removing an amino-protecting group under an acidic condition is known. For example, it may be carried out in a solvent (methylene chloride, dioxane, ethyl acetate, acetic acid, water or mixture thereof etc.), by using an organic acid (e.g., trifluoroacetic acid) or an inorganic acid (HCl, HBr) at 0~120° C.

As for an amino-protecting group which may be removed under an acidic condition, for example, t-butoxycarbonyl is included.

(2) In the present invention compounds of the formula (I), a compound wherein $R^1$ is $NR^6R^7$ in which each $R^6$ and $R^7$ is, independently, hydrogen or C1~4 alkyl, i.e., a compound of the formula (Ib)

(Ib)

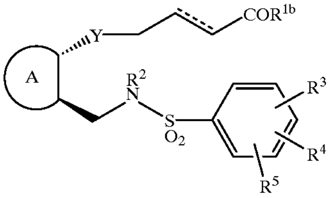

wherein, $R^{1b}$ is $NR^6R^7$ in which each $R^6$ and $R^7$ is, independently, hydrogen or C1~4 alkyl, and the other symbols are the same meaning as defined hereinbefore may be prepared by reacting a compound wherein $R^1$ is hydroxy in the formula (I), i.e., a compound of the formula (Ic)

(Ic)

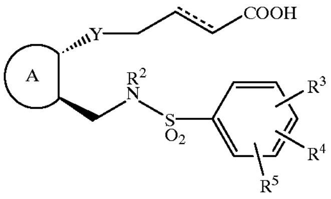

wherein, all symbols are the same meaning as defined hereinbefore with a compound of the formula (IV)

$NHR^6R^7$ (IV)

in which all symbols are the same meaning as defined hereinbefore to form amide bond.

The reaction to form amide bond may be carried out by the procedure as described hereinbefore.

The compounds of the formula (II) and (XI) may be prepared by the procedure as described in the specification of Japanese Patent Application Kokai Hei 6-279395 (U.S. Pat. No. 5,663,417 or European Patent Publication No. 608,847), Japanese Patent Application Kokai Hei 2-180862 (U.S. Pat. No. 5,168,101 or European Patent Publication No. 312,906), Japanese Patent Application Kokai Sho 63-139161 (U.S. Pat. No. 4,861,913 or European Patent Publication No. 226,346) or the following Reaction Scheme (A) to (E).

The symbols in the Reaction Scheme (A) to (E) are the same meaning as defined hereinbefore or as follows:

$Z^1$:hydroxy-protecting group containing silyl group,

Ph:phenyl,

LiHMDS:lithium hexamethyldisilazido, $(PhSe)_2$:diphenyl diselenide,

TBAF:tetrabutylamonium fluoride, $LiAlH_4$:Lithium aluminum hydride,

TsCl:tosylchloride, aq. KOH:aqueous solution of potassium hydroxide,

Ph3P:triphenylphosphine,

DEAD:diethyl azodicarboxylate, $X^1$:halogen, $R^{20}$:C1~4 alkyl, $Z^2$:amino-protecting group which may be removed under an acidic condition.

Reaction Scheme (A)
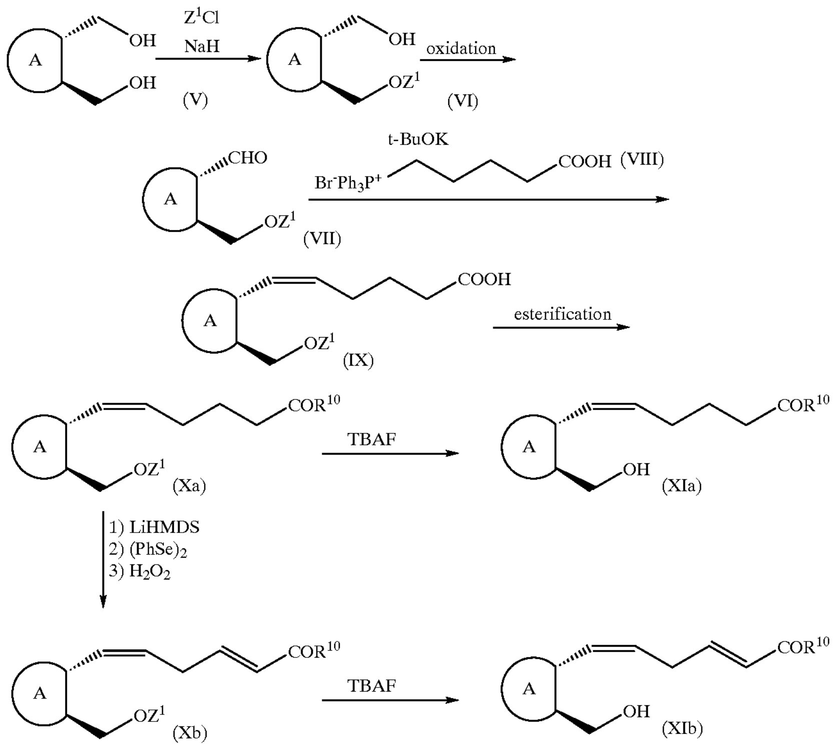
Reaction Scheme (B)
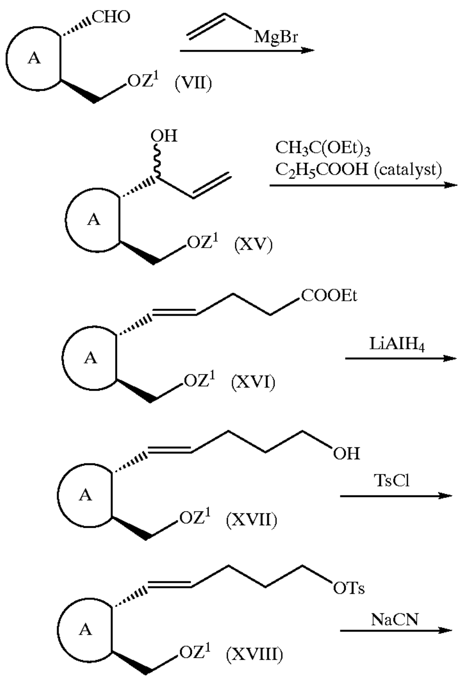
-continued
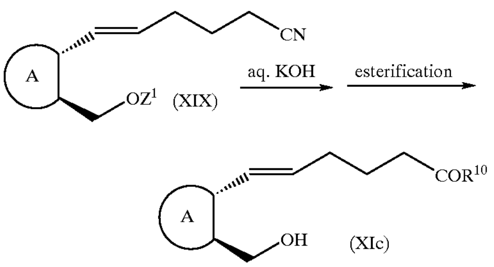

Reaction Scheme (C)

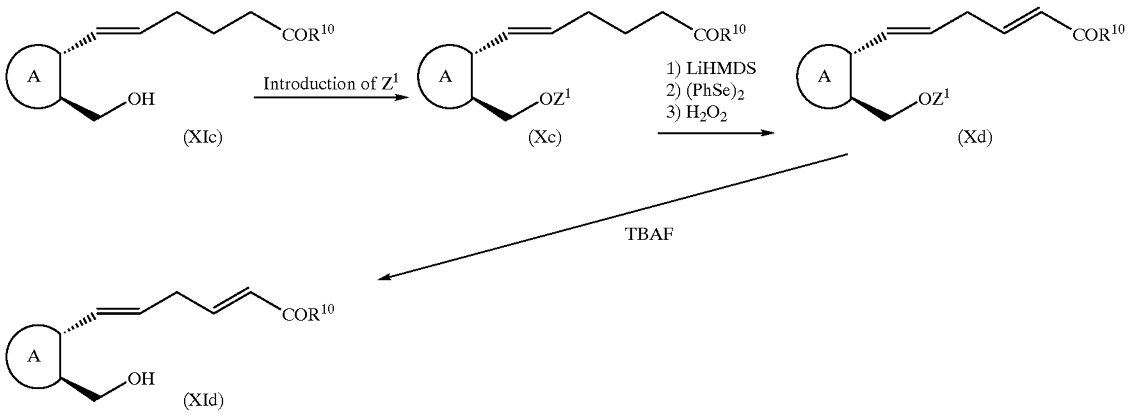

(XIc)
(Xc)
(Xd)
(XId)

Reaction Scheme (D)

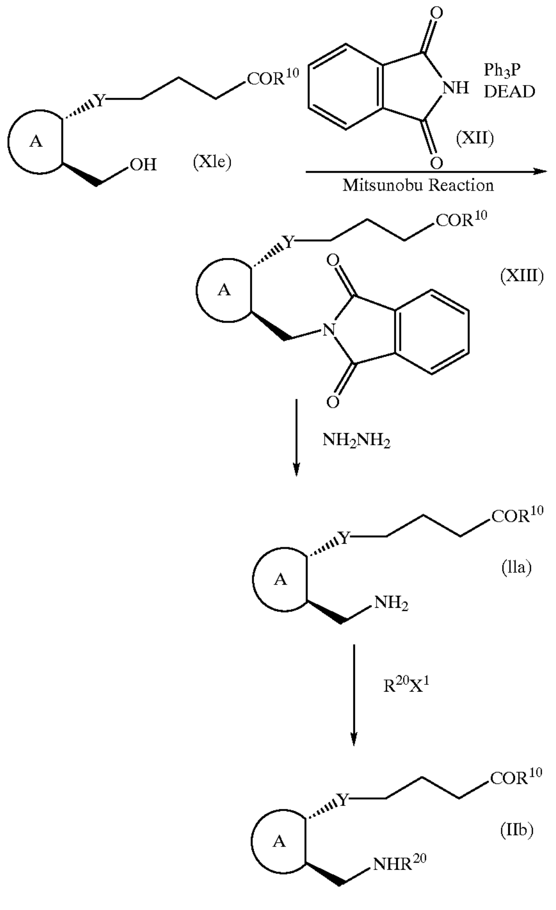

(XIe)
(XII)
(XIII)
(IIa)
(IIb)

-continued

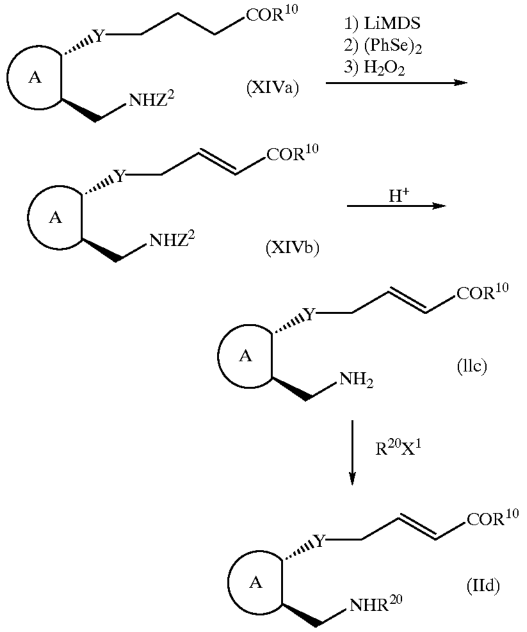

(XIVa)
(XIVb)
(IIc)
(IId)

Reaction Scheme (E)

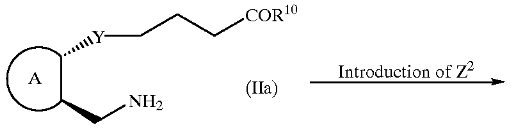

(IIa)

Starting Materials and Reagents

The starting materials and reagents in the present invention are known per se or may be prepared by known methods. The compounds of the formula (V), (VIII), (IV) are known per se or may be prepared by known methods. In the compounds of the formula (III), for example, 2,4-dichlorobenzenesulfonylchloride is available in the market. The compounds of the formula (III-A) may be prepared by reacting the compounds of the formula (III) with ammonia and then introducing an alkyl group or an amino-protecting group which may be removed under an acidic condition ($Z^a$).

In each reaction in the present specification, obtained products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization. Purification may be carried out after each reaction, or after a series of reactions.

Pharmacological Activity of the Present Invention Compounds

The present invention compounds of the formula (I) can bind strongly to EP1 receptor which is a subtype receptor of prostaglandin $E_2$ and show antagonistic activity. As mentioned hereinbefore, it is known that EP1 receptor relates to inducing pain, fever or diuresis. The compounds of the formula (I), non-toxic salts thereof and cyclodextrin clathrate thereof which antagonize against this receptor is considered to be useful as analgesics, as antipyretic agent or as treating agent for pollakiuria. In addition, the present invention compounds scarcely bind to the other subtypes of $PGE_2$ receptor. Therefore, they are considered to not relate to the other various activities of $PGE_2$ and expected to become agent having little side effect.

For example, in standard laboratory test, it was confirmed that they showed such activities according to assay using expression cell of prostanoid receptor subtype.

(i) Binding Assay Using Expression Cell of Prostanoid Receptor Subtype

The preparation of membrane fraction was carried out according to the method of Sugimoto et al (J. Biol. Chem. 267, 6463–6466 (1992)), using expression CHO cell of prostanoid receptor subtype (mouse EP1 and EP3).

The standard assay mixture contained membrane fraction (0.5 mg/ml), $^3H$-$PGE_2$ in a final volume of 200 microliter was incubated for 1 hour at room temperature. The reaction was terminated by addition of 3 ml of ice-cold buffer. The mixture was rapidly filtered through a glass filter (GF/B). The radioactivity associated with the filter was measured by liquid scintillation counting.

Kd and Bmax values were determined from Scatchard plots (Ann. N.Y. Acad. Sci., 51, 660 (1949)). Non-specific binding was calculated as the binding in the presence of an excess (2.5 microM) of unlabeled $PGE_2$. In the experiment for competition of specific $^3H$-$PGE_2$ binding by the compounds of the present invention, $^3H$-$PGE_2$ (2.5 nM) and the present invention compounds were added. The following buffer was used in all reaction. Buffer:potassium phosphate (pH6.0, 10 mM), EDTA (1 mM), $MgCl_2$ (10 mM), NaCl (0.1M).

The dissociation constant Ki (microM) of each compound was calculated by the following equation.

$$Ki=IC50/(1+([C]/Kd))$$

The results are shown in Table 1.

TABLE 1 dissociation constant to receptor subtype of the present invention compounds (Ki, microM)

| Example No. | EP1 | EP3 |
|---|---|---|
| 2 | 0.0005 | 0.12 |
| 2(c) | 0.0018 | 0.20 |
| 2(d) | 0.0014 | 0.085 |
| 2(g) | 0.0034 | 0.95 |
| 2(k) | 0.0024 | 1.4 |
| 2(n) | 0.0051 | 1.9 |
| 3(a) | 0.0031 | 0.018 |
| 3(e) | 0.0084 | 0.11 |
| 3(f) | 0.0011 | 0.041 |
| 4(b) | 0.017 | 0.052 |
| 4(c) | 0.039 | 0.18 |
| 4(f) | 0.0057 | 0.012 |
| 5(a) | 0.012 | 0.28 |
| 5(d) | 0.023 | 1.2 |
| 5(e) | 0.0072 | 0.20 |

TABLE 1-continued dissociation constant to receptor subtype of the present invention compounds (Ki, microM)

| Example No. | EP1 | EP3 |
|---|---|---|
| 6(a) | 0.0039 | 0.37 |
| 6(e) | 0.0042 | 1.1 |
| 7(d) | 0.0039 | 1.4 |
| 7(f) | 0.0072 | 1.5 |

In addition, the same experiment was carried out about the compounds (each structure is shown as hereinafter.) described concretely as $PGE_2$ receptor antagonist or agonist in U.S. Pat. No. 5,663,417 (European Patent Publication No. 608,847, Japanese Patent Application Kokai Hei 6-279395) (called as Related Art (1) hereinafter.) and the compounds described concretely as $TXA_2$ antagonist in U.S. Pat. No. 5,168,101 (European Patent Publication No. 312,906, Japanese Patent Application Kokai Hei 2-180862) (called as Related Art (2) hereinafter.). The results are shown in Table 2.

TABLE 2 dissociation constant to receptor subtype of the compounds of Related Arts (1) and (2) (Ki, microM)

| Example No. or order in Table 1 of Related Art (1) | EP1 | EP3 |
|---|---|---|
| Example 5(d) | 1.3 | 0.17 |
| Example 6-17 | >10 | 0.0027 |
| Example 6-19 | 2.3 | 0.013 |
| 31st Compound in Table 1 | 0.069 | 0.095 |
| **Example. No. of Related Art (2)** | **EP1** | **EP3** |
| Example 1(p) | 0.46 | 0.29 |
| Example 1(aa) | 3.6 | 0.48 |
| Example 1(bb) | 0.19 | 0.14 |

The structure of the compounds described concretely in the corresponding examples or Table 1 of Related Art (1) (U.S. Pat. No. 5,663,417, European Patent Publication No. 608,847, Japanese Patent Application Kokai Hei 6-279395) in the above Table 2 is as follows:

Example 5(d):

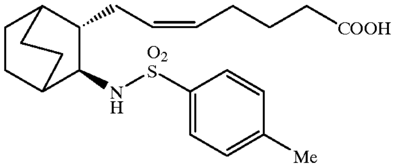

Example 6-17:

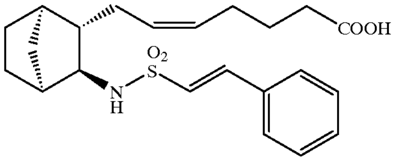

-continued

Example 6-19:

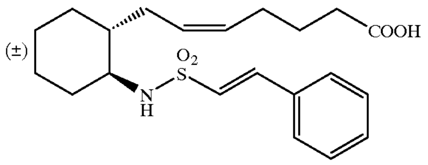

The 31st compound in Table 1:

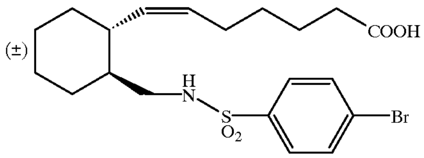

The structure of the compounds described concretely in the corresponding examples of Related Art (2) (U.S. Pat. No. 5,168,101, European Patent Publication No. 312,906, Japanese Patent Application Kokai Hei 2-180862) in the above Table 2 is as follows:

Example 1(p):

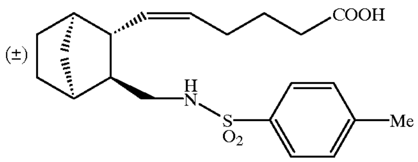

Example 1(aa):

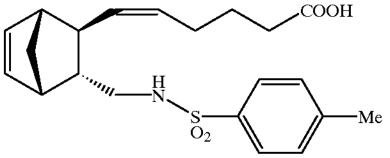

Example 1(bb):

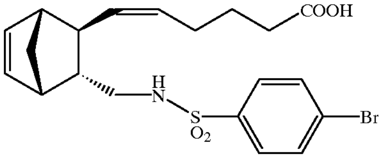

The data of Tables 1 and 2 showed that the present invention compounds of the formula (I) possess the superior activity with respect to the strength and selectivity in binding onto EP1 receptor compared with the compounds of U.S. Pat. No. 5,663,417 (Related Art (1), European Patent Publication No. 608,847, Japanese Patent Application Kokai Hei 6-279395) and U.S. Pat. No. 5,168,101 (Related Art (2), European Patent Publication No. 312,906, Japanese Patent Application Kokai Hei 2-180862).

Toxicity

The toxicity of the compounds of the present invention is very low and therefore, it is confirmed that these compounds are safe for use as medicine.

Application for Pharmaceuticals

For the purpose above described, the present invention compounds of the formula (I), non-toxic salts thereof or cyclodextrin clathrate thereof may be normally administered systematically or partially, usually by oral or parenteral administration.

The doses to be administered are determined depending upon age, body weight, symptom, the desired therapeutic effect, the route of administration, and the duration of the treatment etc. In the human adult, the doses per person per dose are generally between 1 mg and 100 mg, by oral administration, up to several times per day, and between 0.1 mg and 10 mg, by parenteral administration (preferred into vein) up to several times per day, or continuous administration between 1 and 24 hrs. per day into vein.

As mentioned above, the doses to be used depend upon various conditions. Therefore, there are cases in which doses lower than or greater than the ranges specified above may be used.

When administration of the compounds of the present invention, it is used as inner solid compositions, inner liquid compositions and the other compositions for oral administration, or as injections, liniments or suppositories etc. for parenteral administration.

Inner solid compositions for oral administration include tablets, pills, capsules, dispersible powders, and granules etc.

Capsules contain hard capsules and soft capsules.

In such inner solid compositions, one or more of the active compound(s) is or are, admixed with at least one inert diluent e.g. lactose, mannitol, mannit, glucose, hydroxypropyl cellulose, microcrystalline cellulose, starch, polyvinylpyrrolidone, magnesium metasilicate aluminate etc. Such a compositions may contain additional substances other than inert diluent, for example, lubricating agents e.g. magnesium stearate, disintegrating agents e.g. cellulose calcium glycolate, assisting agents for dissolving e.g. glutamic acid, asparaginic acid by known methods. Tablets or pills may, if desired, be coated with gastric or enteric films such as sugar, gelatin, hydroxypropyl cellulose or hydroxypropyl cellulose phthalate etc., or be coated with two or more films. And further, the compositions also include capsules of absorbable materials such as gelatin.

Inner liquid compositions for oral administration include pharmaceutically-acceptable emulsions, solutions, syrups and elixirs etc. In such liquid compositions, one or more of the active compound(s) is or are comprised in inert diluent (s) commonly used in the art (purified water, ethanol). Besides inert diluents, such compositions may also comprise adjuvants such as wetting agents, suspending agents, sweetening agents, flavouring agents, perfuming agents, preserving agents.

Other compositions for oral administration include spray compositions which may be prepared by known methods and which comprise one or more of the active compound(s). Spray compositions may comprise additional substances other than inert diluents: e.g. stabilizing agents such as sodium hydrogen sulfate, stabilizing agents to give isotonicity, isotonic buffer such as sodium chloride, sodium citrate, citric acid. For preparation of such spray compositions, for example, the method described in the U.S. Pat. No. 2,868,691 or 3,095,355 may be used.

Injections for parenteral administration of the present invention include sterile aqueous or non-aqueous solutions, suspensions and emulsions. Aqueous solutions or suspensions include distilled water for injection and physiological salt solution. Non-aqueous solutions or suspensions include propylene glycol, polyethylene glycol, plant oil such as olive oil, alcohol such as ethanol, POLYSOLBATE80 (registered trade mark) etc. Such compositions may comprise additional diluents: e.g. preserving agents, wetting agents, emulsifying agents, dispersing agents, stabilizing agent, assisting agents such as assisting agents for dissolving (for example, glutamic acid, asparaginic acid). They may be sterilized for example, by filtration through a bacteria-retaining filter, by incorporation of sterilizing agents in the compositions or by irradiation. They also be manufactured in the form of sterile solid compositions and which can be dissolved in sterile water or some other sterile diluents for injection immediately before used.

Other compositions for parenteral administration include liquids for external use, and endemic liniments, ointment, suppositories for rectal administration and pessaries for vaginal administration which comprise one or more of the active compound(s) and may be prepared by know methods.

REFERENCE EXAMPLES AND EXAMPLES

The following Reference examples and Examples are intended to illustrate, but not limit, the present invention. The solvents in parentheses show the developing or eluting solvents and the ratios of the solvents used are by volume in chromatographic separations.

Example 1

6-[(2S, 3S)-3-(2,4-dichlorophenylsulfonylaminomethyl) bicyclo[2.2.2]octan-2-yl]-5Z-hexenoic acid methyl ester

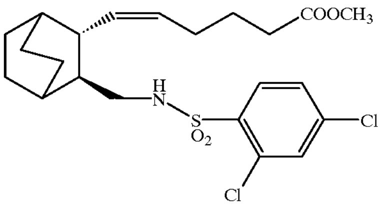

To a solution of 6-[(2S, 3S)-3-aminomethylbicyclo[2.2.2] octan-2-yl]-5Z-hexenoic acid methyl ester (1.70 g) in methylene chloride (30 ml), triethylamine (2.6 ml) was added. A solution of 2,4-dichlorobenzene-sulfonylchloride (2.04 g) in methylene chloride (10 ml) was dropwise thereto. The solution was stirred for 1 hour at 0° C. After the termination of reaction, the solution was quenched by adding 1N HCl and extracted with ethyl acetate. The organic layer was washed with water and saturated saline solution succeedingly, dried over anhydrous sodium sulfate and concentrated under the reduced pressure to give the crude compound. This crude compound was purified with column chromatography (ethyl acetate-hexane) to give the title compound (1.842 g) having the following physical data as colorless viscous oil.

TLC: Rf 0.55 (AcOEt:hexane=1:2);

NMR ($CDCl_3$): δ 8.03 (1 H, d, J=8 Hz), 7.55 (1 H, d, J=2 Hz), 7.40 (1 H, dd, J=8, 2 Hz), 5.50–5.22 (2 H, m), 5.00 (1 H, t, J=5 Hz), 3.67 (3 H, s), 2.97–2.72 (2 H, m), 2.30 (2 H, t, J=7 Hz), 2.12–1.87 (3 H, m), 1.80–1.20 (13 H, m).

Example 2

6-[(2S, 3S)-3-(2,4-dichlorophenylsulfonylaminomethyl) bicyclo[2.2.2]octan-2-yl]-5Z-hexenoic acid

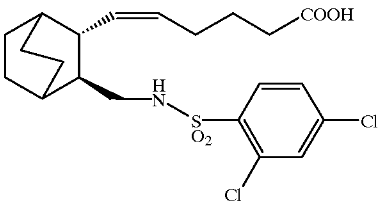

A compound prepared in Example 1 was dissolved in methanol (10 ml) and dimethoxyethane (20 ml). To this solution, 2N sodium hydroxide aqueous solution (5 ml) was added at room temperature. The solution was stirred at room temperature overnight. After the termination of reaction, to the reaction solution, 2N HCl was added at room temperature. The solution was extracted with ethyl acetate. The organic layer was washed with water and saturated saline solution succeedingly, dried over anhydrous sodium sulfate, filtrated and concentrated under the reduced pressure to give the crude compound. This crude compound was purified with column chromatography (methanol/methylene chloride) to give the title compound (1.44 g) having the following physical data.

TLC: Rf 0.26 (hexane:AcOEt=2:3);

NMR ($CDCl_3$): δ 8.02 (1H, d, J=8.5 Hz), 7.54 (1H, d, J=2 Hz), 7.40 (1H, dd, J=8.5 and 2 Hz), 5.50–5.24 (2H, m), 5.07 (1H, t, J=6 Hz), 2.84 (2H, m), 2.35 (2H, t, J=7 Hz), 2.18–1.92 (3H, m), 1.79–1.21 (13H, m).

Example 2(a)~2(n)

By the same procedure as Examples 1 and 2, the title compounds having the following physical data were obtained.

Example 2(a)

6-[(2S, 3S)-3-(2,4-dimethylphenylsulfonylaminomethyl) bicyclo[2.2.2]octan-2-yl]-5Z-hexenoic acid

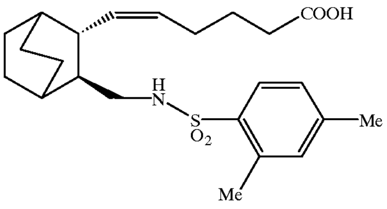

TLC: Rf 0.09 (hexane:AcOEt=1:1);

NMR ($CDCl_3$): δ 7.83 (1H, d, J=8.4 Hz), 7.1 (2H, m), 5.5–5.3 (2H, m), 4.66 (1H, t, J=6 Hz), 3.0–2.7 (2H, m), 2.58 (3H, s), 2.38 (3H, s), 2.36 (2H, t), 2.2–1.9 (m), 1.8–1.2 (m).

Example 2(b)

6-[(2S, 3S)-3-(2,4-dibromophenylsulfonylaminomethyl) bicyclo[2.2.2]octan-2-yl]-5Z-hexenoic acid

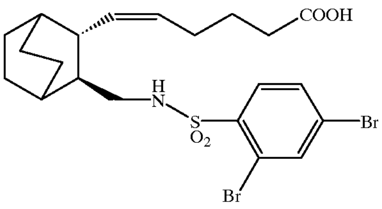

TLC: Rf 0.41 (AcOEt);

NMR ($CDCl_3$): δ 7.99 (1H, d, J=8.5H), 7.90 (1H, d, J=2 Hz), 7.61 (1H, dd, J=8.5 and 2H), 5.51–5.23 (2H, m), 5.16 (1H, t, J=6 Hz), 2.95–2.67 (2H, m), 2.35 (2H, t, J=7 Hz), 2.15–1.90 (3H, m), 1.78–1.20 (13H, m).

Example 2(c)

6-[(2S, 3S)-3-(4-chloro-2-methylphenylsulfonylaminomethyl)bicyclo[2.2.2]octan-2-yl]-5Z-hexenoic acid

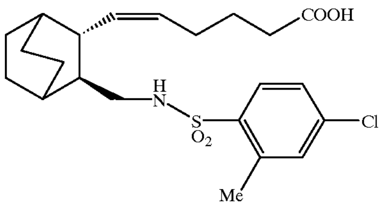

TLC: Rf 0.51 ($CHCl_3$:MeOH:AcOH=100:5:1);

NMR ($CDCl_3$): δ 7.88 (1H, d, J=9.0 Hz), 7.26–7.31 (2H, m), 5.25–5.51 (2H, m), 4.80 (1H, t, J=5.8 Hz), 2.86 (2H, m), 2.59 (3H, s), 2.36 (2H, t, J=7.4 Hz), 1.92–2.18 (3H, m), 1.20–1.82 (13H, m).

Example 2(d)

6-[(2S, 3S)-3-(4-bromo-2-methylphenylsulfonylaminomethyl)bicyclo[2.2.2]octan-2-yl]-5Z-hexenoic acid

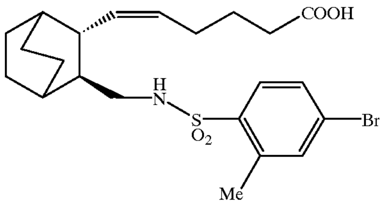

TLC: Rf 0.53 (AcOEt:hexane:AcOH=5:14:1);

NMR ($CDCl_3$): δ 7.81 (1H, d, J=9.0Hz), 7.48 (1H, s), 7.46 (1H, d, J=9.0 Hz), 5.55–5.25 (2H, m), 4.80 (1H, t, J=6.0 Hz), 3.00–2.70 (2H, m), 2.59 (3H, s), 2.36 (2H, t, J=7.0 Hz), 2.20–1.90 (3H, m), 1.72 (2H, q, J=7.0 Hz), 1.80–1.10 (11H, m).

Example 2(e)

6-[(2S, 3S)-3-(4-bromo-2-fluorophenylsulfonylaminomethyl)bicyclo[2.2.2]octan-2-yl]-5Z-hexenoic acid

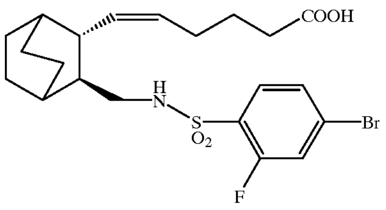

TLC: Rf 0.42 (AcOEt);

NMR ($CDCl_3$): δ 7.76 (1H, m), 7.48–7.35 (2H, m), 5.52–5.25 (2H, m), 4.91 (1H, d, J=6 Hz), 2.92 (2H, m), 2.36 (2H, t, J=7 Hz), 2.16–1.93 (3H, m), 1.82–1.20 (13H, m).

Example 2(f)

6-[(2S, 3S)-3-(4-chloro-2-fluorophenylsulfonylaminomethyl)bicyclo[2.2.2]octan-2-yl]-5Z-hexenoic acid

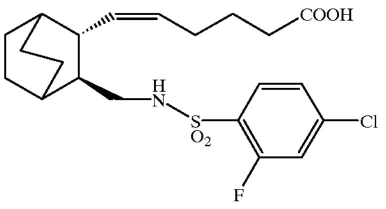

TLC: Rf 0.41 (AcOEt);

NMR ($CDCl_3$): δ 7.84 (1H, m), 7.34–7.20 (2H, m), 5.53–5.24 (2H, m), 4.91 (1H, d, J=6 Hz), 2.92 (2H, m), 2.36 (2H, t, J=7.5 Hz), 2.17–1.93 (3H, m), 1.81–1.20 (13H, m).

Example 2(g)

6-[(2S, 3S)-3-(2,4,6-trichlorophenylsulfonylaminomethyl) bicyclo[2.2.2]octan- 2-yl]-5Z-hexenoic acid

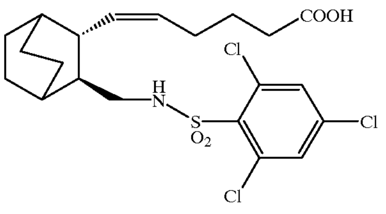

TLC: Rf 0.53 (AcOEt:hexane:AcOH=5:14:1);

NMR ($CDCl_3$): δ 7.49 (2H, s), 5.55–5.25 (3H, m), 3.10–2.80 (2H, m), 2.36 (2H, t, J=7.0 Hz), 2.20–1.95 (3H, m), 1.80–1.20 (13H, m).

Example 2(h)

6-[(2S, 3S)-3-(2-chloro-4-methylphenylsulfonylaminomethyl)bicyclo[2.2.2]octan-2-yl]-5Z-hexenoic acid

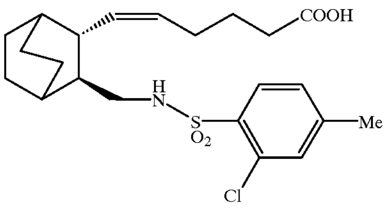

TLC: Rf 0.45 (AcOEt:hexane:AcOH=5:14:1);

NMR ($CDCl_3$): δ 7.96 (1H, d, J=8.0 Hz), 7.34 (1H, d, J=1.0 Hz), 7.21 (1H, dd, J=8.0, 1.0 Hz), 5.50–5.22 (2H, m), 5.01 (1H, t, J=6.0 Hz), 2.95–2.67 (2H, m), 2.41 (3H, s), 2.34 (2H, t, J=7.0 Hz), 2.15–1.90 (3H, m), 1.80–1.60 (2H, q, J=7.5 Hz), 1.80–1.20 (11H, m).

Example 2(i)

6-[(2S, 3S)-3-(4-chloro-2-trifluoromethylphenylsulfonylaminomethyl)bicyclo-[2.2.2] octan-2-yl]-5Z-hexenoic acid

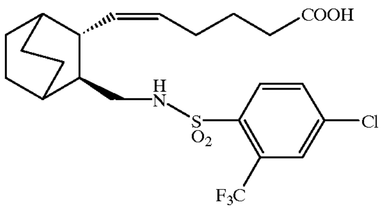

TLC: Rf 0.24 (hexane:AcOEt:=1:1);

NMR ($CDCl_3$): δ 8.08 (1H, d, J=8.6 Hz), 7.77 (1H, d, J=2 Hz), 7.60 (1H, dd, J=8.6, 2 Hz), 5.4–5.2 (2H, m), 4.75 (1H, t, J=5.4 Hz), 2.9–2.7 (2H, m), 2.28 (2H, t, J=7.2 Hz), 2.1–1.9 (3H, m), 1.7–1.2 (13H, m).

Example 2(j)

6-[(2S, 3S)-3-(2,4,6-trimethylphenylsulfonylaminomethyl)bicyclo[2.2.2]octan-2-yl]-5Z-hexenoic acid

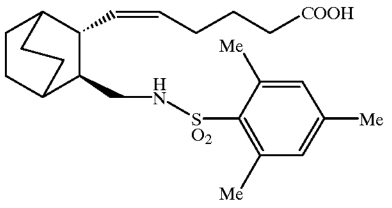

TLC: Rf 0.51 (AcOEt:hexane:AcOH=5:14:1);

NMR ($CDCl_3$): δ 6.95 (2H, s), 5.52–5.17 (2H, m), 4.64 (1H, t, J=6.0 Hz), 2.98–2.65 (2H, m), 2.62 (6H, s), 2.35 (2H, t, J=6.0 Hz), 2.30 (3H, s), 2.17–1.90 (3H, m), 1.70 (2H, q, J=7.0 Hz), 1.80–1.20 (11H, m).

Example 2(k)

6-[(2S, 3S)-3-(2,4-dichloro-6-methylphenylsulfonylaminomethyl)bicyclo[2.2.2]octan-2-yl]-5Z-hexenoic acid

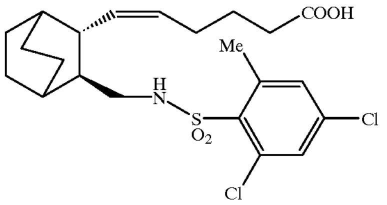

TLC: Rf 0.45 (AcOEt);

NMR ($CDCl_3$): δ 7.40 (1H, d, J=2 Hz), 7.24 (1H, d, J=2 Hz), 5.50–5.24 (3H, m), 2.99–2.73 (2H, m), 2.69 (3H, s), 2.34 (2H, t, J=7 Hz), 2.16–1.90 (3H, m), 1.77–1.23 (13H, m).

Example 2(l)

6-[(2S, 3S)-3-(4-chloro-2,6-dimethylphenylsulfonylaminomethyl)bicyclo[2.2.2]-octan-2-yl]-5Z-hexenoic acid

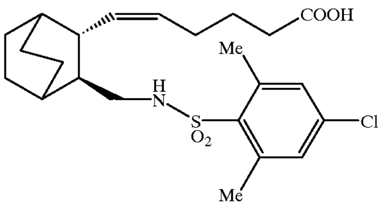

TLC: Rf 0.47 (AcOEt);

NMR ($CDCl_3$): δ 7.15 (2H, s), 5.51–5.23 (2H, m), 4.74 (1H, t, J=6 Hz), 2.98–2.70 (2H, m), 2.63 (6H, s), 2.35 (2H, t, J=7 Hz), 2.16–1.90 (3H, m), 1.80–1.22 (13H, m).

Example 2(m)

6-[(2S, 3S)-3-(2,4-dichlorophenylsulfonylaminomethyl)bicyclo[2.2.2]octan-2-yl]-5E-hexenoic acid

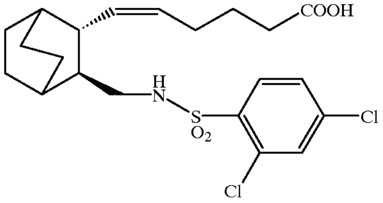

TLC: Rf 0.24 (AcOE:Hexane=3:2);

NMR ($CDCl_3$): δ 8.03 (1H, d, J=8 Hz), 7.54 (1H, d, J=8 Hz), 7.40(1H, dd, J=8, 2 Hz), 5.53–5.27 (3H, m), 3.00–2.83 (1H, m), 2.83–2.67 (1H, m), 2.50–2.20 (2H, m), 2.17–2.00 (2H, m), 1.83–1.20 (14H, m).

Example 2(n)

6-[(2S, 3S)-3-(4-chloro-2-methylphenylsulfonylaminomethyl)bicyclo[2.2.2]-octan-2-yl]-5E-hexenoic acid

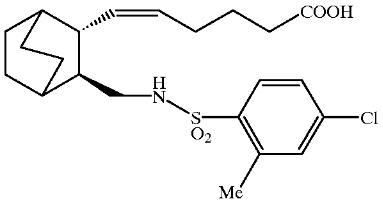

TLC: Rf 0.37 (AcOE:Hexane=3:2);

NMR ($CDCl_3$): δ 7.89 (1H, d, J=8 Hz), 7.33 (1H, s), 7.30(1H, d, J=8 Hz), 5.58–5.30 (3H, m), 3.06–2.86(1H, m), 2.80–2.58 (1H, m), 2.62 (3H, s), 2.51–2.00 (4H, m), 1.90–1.20 (14H, m).

Example 3(a)~3(h)

By the same procedure as Examples 1 and 2, the title compounds having the following physical data were obtained.

Example 3(a)

6-[(1R, 2S)-2-(2,4-dichlorophenylsulfonylaminomethyl)cyclohexyl]-5Z-hexenoic acid

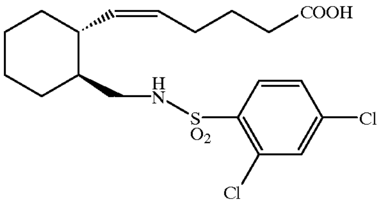

TLC: Rf 0.44 (AcOEt:hexane:AcOH=5:14:1);

NMR ($CDCl_3$): δ 8.00 (1H, d, J=8.5 Hz), 7.53 (1H, d, J=2.0 Hz), 7.39 (1H, dd, J=8.5, 2.0 Hz), 5.34 (1H, dt, J=11.0, 7.0 Hz), 5.15 (1H, t, J=1.0 Hz), 5.10 (1H, t, J=6.0 Hz), 2.90 (1H, ddd, J=13.0, 6.0, 4.5 Hz), 2.64 (1H, dt, J=1 3.0, 7.0 Hz), 2.33 (2H, t, J=7.0 Hz), 2.15–1.85 (3H, m), 1.85–1.40 (6H, m), 1.40–0.80 (5H, m).

Example 3(b)

6-[(1R, 2S)-2-(4-bromo-2-fluorophenylsulfonylaminomethyl)cyclohexyl]-5Z-hexenoic acid

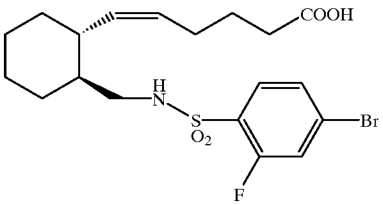

TLC: Rf 0.55 (MeOH:$CHCl_3$=1:5);

NMR ($CDCl_3$): δ 7.75 (1H, t, J=8 Hz), 7.47–7.33 (2H, m), 5.43–5.10 (2H, m), 4.93 (1H, t, J=6 Hz), 3.05–2.90 (1H, m), 2.82–2.60 (1H, m), 2.36 (2H, t, J=7 Hz), 2.16–1.86 (3H, m), 1.86–0.80 (11H, m).

Example 3(c)

6-[(1R, 2S)-2-(4-bromo-2-methylphenylsulfonylaminomethyl)cyclohexyl]-5Z-hexenoic acid

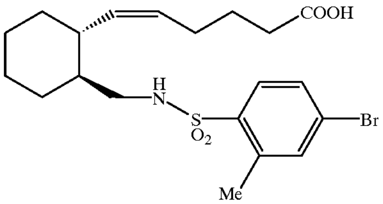

TLC: Rf 0.58 (MeOH:$CHCl_3$=1:5);

NMR ($CDCl_3$): δ 7.78 (1H, d, J=8 Hz), 7.47 (1H, s), 7.45 (1H, d, J=8 Hz), 5.43–5.05 (2H, m), 4.75 (1H, m), 3.00–2.80 (1H, m), 2.80–2.46 (1H, m), 2.60 (3H, s), 2.34 (2H, t, J=7 Hz), 2.17–1.80 (3H, m), 1.80–0.80 (10H, m).

Example 3(d)

6-[(1R, 2S)-2-(4-chloro-2-fluorophenylsulfonylaminomethyl)cyclohexyl]-5Z-hexenoic acid

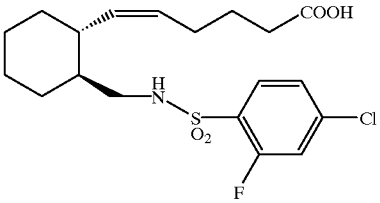

TLC: Rf 0.54 (MeOH:$CHCl_3$=1:5);

NMR ($CDCl_3$): δ 7.81 (1H, t, J=8 Hz), 7.33–7.18 (2H, m), 5.44–5.05 (2H, m), 4.93 (1H, t, J=7 Hz), 3.08–2.90 (1H, m), 2.84–2.63 (1H, m), 2.33 (2H, t, J=7 Hz), 2.20–1.87 (4H, m), 1.87–0.80 (10H, m).

Example 3(e)

6-[(1R, 2S)-2-(2,4,6-trichlorophenylsulfonylaminomethyl)cyclohexyl]-5Z-hexenoic acid

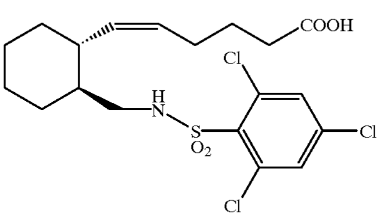

TLC: Rf 0.59 (MeOH:$CHCl_3$=1:5);

NMR ($CDCl_3$): δ 7.48 (1H, s), 5.47–5.10 (3H, m), 3.10–2.93 (1H, m), 2.87–2.60 (1H, m), 2.34 (2H, t, J=7 Hz), 2.17–1.88 (3H, m), 1.88–0.80 (11H, m).

Example 3(f)

6-[(1R, 2S)-2-(4-chloro-2-methylphenylsulfonylaminomethyl)cyclohexyl]-5Z-hexenoic acid

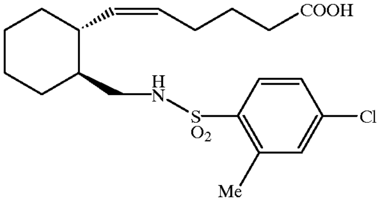

TLC: Rf 0.56 (MeOH:$CHCl_3$=1:5);

NMR ($CDCl_3$): δ 7.88 (1H, d, J=8 Hz), 7.32 (1H, s), 7.35–7.24 (1H, m), 5.47–5.10 (2H, m), 4.74 (1H, m), 3.06–2.83 (1H, m), 2.80–2.50 (1H, m), 2.63 (3H, s), 2.35 (2H, t, J=7 Hz), 2.15–0.80 (14H, m).

Example 3(g)

6-[(1R, 2S)-2-(4-chloro-2,6-dimethylphenylsulfonylaminomethyl)cyclohexyl]-5Z-hexenoic acid

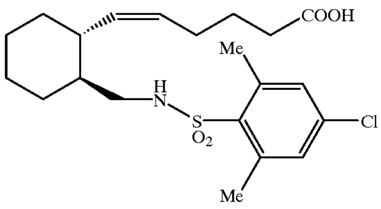

TLC: Rf 0.25 ($MeOH:CHCl_3$=1:10);

NMR ($CDCl_3$): δ 7.15 (2H, s), 5.43–5.22 (1H, m), 5.22–5.05 (1H, m), 4.74 (1H, m), 3.00–2.80 (1H, m), 2.77–2.45 (1H, m), 2.63 (6H, s), 2.33 (2H, t, J=7 Hz), 2.20–1.83 (3H, m), 1.83–1.33 (7H, m), 1.33–0.80 (4H, m).

Example 3(h)

6-[(1R, 2S)-2-(2,4-dichloro-6-methylphenylsulfonylaminomethyl)cyclohexyl]-5Z-hexenoic acid

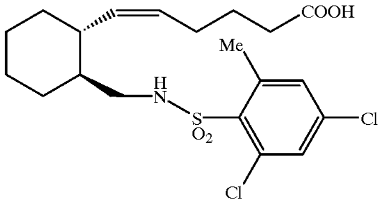

TLC: Rf 0.28 ($MeOH:CHCl_3$=1:10);

NMR ($CDCl_3$): δ 7.40 (1H, d, J=2 Hz), 7.23 (1H, d, J=2 Hz), 5.47–5.25 (2H, m), 5.15 (1H, t, J=10 Hz), 3.00–2.83 (1H, m), 2.80–2.50 (1H, m), 2.68 (3H, s), 2.33 (2H, t, J=7 Hz), 2.20–1.87 (3H, m), 1.87–1.35 (7H, m), 1.35–0.80 (4H, m).

Example 4(a)~4(h)

By the same procedure as Examples 1 and 2, the title compounds having the following physical data were obtained.

Example 4(a)

6-[(4R, 5S)-5-(2,4-dichlorophenylsulfonylaminomethyl) cyclohexen-4-yl]-5Z-hexenoic acid

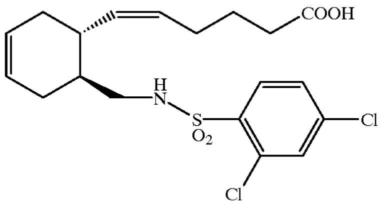

TLC: Rf 0.63 ($CHCl_3$:MeOH:AcOH=100:5:1);

NMR ($CDCl_3$); δ 8.01 (1H, d, J=8.4 Hz), 7.54 (1H, d, J=2.0 Hz), 7.39 (1H, dd, J=2.0, 8.4 Hz), 5.63 (2H, m), 5.22–5.48 (2H, m), 5.18 (1H, t, J=6.6 Hz), 2.97 (1H, m), 2.73 (1H, m), 2.29–2.50 (3H, m), 1.92–2.29 (4H, m), 1.56–1.92 (5H, m).

Example 4(b)

6-[(4R, 5S)-5-(4-chloro-2-methylphenylsulfonylaminomethyl)cyclohexen-4-yl]-5Z-hexenoic acid

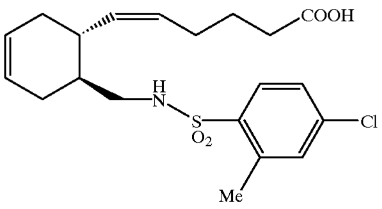

TLC: Rf 0.61 ($CHCl_3$:MeOH:AcOH=100:5:1);

NMR ($CDCl_3$): δ 7.87 (1H, m), 7.29 (2H, m), 5.61 (2H, m), 5.23–5.47 (2H, m), 4.90 (1H, t, J=6.4 Hz), 2.99 (1H, m), 2.74 (1H, m), 2.61 (3H, s), 2.26–2.52 (3H, m), 1.92–2.26 (4H, m), 1.56–1.92 (5H, m).

Example 4(c)

6-[(4R, 5S)-5-(4-chloro-2-fluorophenylsulfonylaminomethyl)cyclohexen-4-yl]-5Z-hexenoic acid

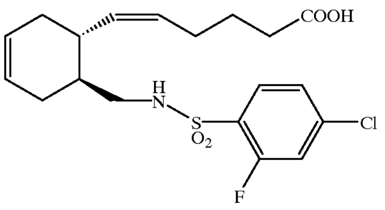

TLC: Rf 0.55 ($CHCl_3$:MeOH:AcOH=100:5:1);

NMR ($CDCl_3$): δ 7.82 (1H, dd, J=8.2, 9.2 Hz), 7.26 (2H, m), 5.63 (2H, m), 5.22–5.47 (2H, m), 5.03 (1H, t, J=6.6 Hz), 3.05 (1H, m), 2.81 (1H, m), 2.29–2.50 (3H, m), 1.94–2.29 (4H, m), 1.56–1.94 (5H, m).

Example 4(d)

6-[(4R, 5S)-5-(4-bromo-2-fluorophenylsulfonylaminomethyl)cyclohexen-4-yl]-5Z-hexenoic acid

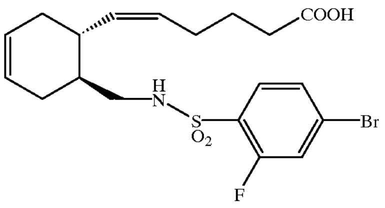

TLC: Rf 0.63 ($CHCl_3$:MeOH:AcOH=100:5:1);

NMR ($CDCl_3$): δ 7.75 (1H, dd, J=8.2, 8.8 Hz), 7.42 (2H, m), 5.63 (2H, m), 5.22–5.47 (2H, m), 5.04 (1H, t, J=6.2 Hz), 3.05 (1H, m), 2.81 (1H, m), 2.29–2.50 (3H, m), 1.92–2.29 (4H, m), 1.58–1.92 (5H, m).

Example 4(e)

6-[(4R, 5S)-5-(2,4,6-trichlorophenylsulfonylaminomethyl) cyclohexen-4-yl]-5Z-hexenoic acid

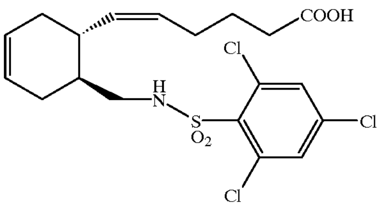

TLC: Rf 0.49 ($CHCl_3$:MeOH:AcOH=100:5:1);

NMR ($CDCl_3$): δ 7.49 (2H, s), 5.64 (2H, m), 5.25–5.50 (3H, m), 3.09 (1H, m), 2.84 (1H, m), 2.28–2.48 (3H, m), 1.93–2.28 (4H, m), 1.60–1.93 (5H, m).

Example 4(f)

6-[(4R, 5S)-5-(4-bromo-2-methylphenylsulfonylaminomethyl)cyclohexen-4-yl]-5Z-hexenoic acid

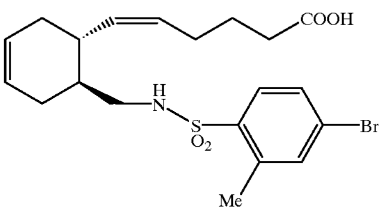

TLC: Rf 0.52 ($CHCl_3$:MeOH:AcOH=100:5:1);

NMR ($CDCl_3$): δ 7.79 (2H, d, J=8.0 Hz), 7.45 (2H, m), 5.61 (2H, m), 5.24–5.47 (2H, m), 4.90 (1H, t, J=6.4 Hz), 2.94 (1H, m), 2.74 (1H, m), 2.60 (3H, s), 2.26–2.48 (3H, m), 1.90–2.26 (4H, m), 1.54–1.90 (5H, m).

Example 4(g)

6-[(4R, 5S)-5-(2,4-dichloro-6-methylphenylsulfonylaminomethyl)cyclohexen-4-yl]-5Z-hexenoic acid

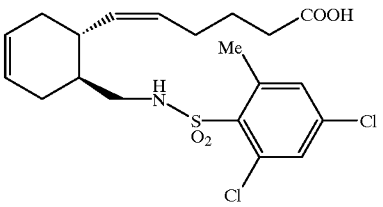

TLC: Rf 0.51 ($CHCl_3$:MeOH:AcOH=100:5:1);

NMR ($CDCl_3$): δ 7.41 (1H, d, J=2.2 Hz), 7.23 (1H, d, J=2.2 Hz), 5.64 (2H, m), 5.22–5.47 (3H, m), 2.98 (1H, m), 2.73 (1H, m), 2.68 (3H, s), 2.28–2.50 (3H, m), 1.92–2.28 (4H, m), 1.56–1.92 (5H, m).

Example 4(h)

6-[(4R, 5S)-5-(4-chloro-2,6-dimethylphenylsulfonylaminomethyl)cyclohexen-4-yl]-5Z-hexenoic acid

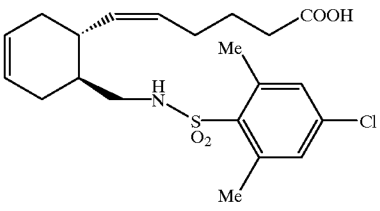

TLC: Rf 0.47($CHCl_3$:MeOH:AcOH=100:5:1);

NMR ($CDCl_3$): δ 7.15 (2H, s), 5.61 (2H, m), 5.22–5.47 (2H, m), 4.86 (1H, t, J=7.0 Hz), 2.97 (1H, m), 2.71 (1H, m), 2.64 (6H, s), 2.27–2.46 (3H, m), 1.90–2.24 (4H, m), 1.57–1.90 (5H, m).

Example 5(a)~5(h)

By the same procedure as Examples 1 and 2, the title compounds having the following physical data were obtained.

Example 5(a)

6-[(1R, 2S, 3S, 4S)-3-(2,4-dichlorophenylsulfonylaminomethyl)bicyclo[2.2.1]-heptan-2-yl]-5Z-hexenoic acid

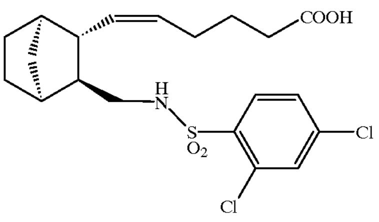

TLC: Rf 0.21 (hexane:AcOEt=2:1);

NMR ($CDCl_3$): δ 8.03 (1H, d, J=8.5 Hz), 7.54 (1H, d, J=2.0 Hz), 7.41 (1H, dd, J=2.0 and 8.5 Hz), 5.26–5.17 (2H, m), 4.95 (1H, t, J=6 Hz), 3.07–2.72 (2H, m), 2.38–2.31 (2H, m), 2.19–2.02 (3H, m), 1.90–1.88 (1H, m), 1.77–1.23 (10H, m).

Example 5(b)

6-[(1R, 2S, 3S, 4S)-3-(4-bromo-2-fluorophenylsulfonylaminomethyl)bicyclo-[2.2.1]heptan-2-yl]-5Z-hexenoic acid

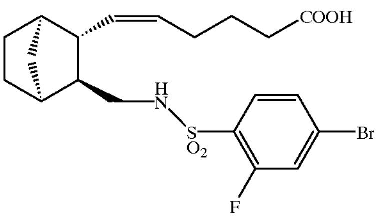

TLC: Rf 0.49 ($CHCl_3$:MeOH:$H_2O$=9:1:0.1);

NMR ($CDCl_3$): δ 7.81–7.73 (1H, m), 7.47–7.38 (2H, m), 5.33–5.14 (2H, m), 4.86 (1H, t-like), 3.12–2.83 (2H, m), 2.34 (2H, t, J=7.4 Hz), 2.19–1.10 (14H, m).

Example 5(c)

6-[(1R, 2S, 3S, 4S)-3-(4-bromo-2-methylphenylsulfonylaminomethyl)bicyclo-[2.2.1]heptan-2-yl]-5Z-hexenoic acid

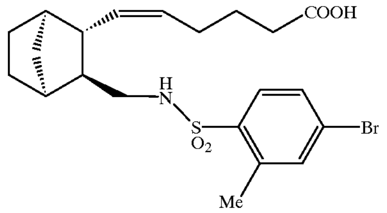

TLC: Rf 0.47 ($CHCl_3$:MeOH:$H_2O$=9:1:0.1);

NMR ($CDCl_3$): δ 7.83 (1H, d, J=9.0 Hz), 7.48–7.43 (2H, m),5.34–5.14 (2H, m), 4.72 (1H, t-like), 3.07–2.75 (2H, m), 2.60 (3H, s), 2.34 (2H, t, J=7.4 Hz), 2.15–1.09 (14H, m).

Example 5(d)

6-[(1R, 2S, 3S, 4S)-3-(4-chloro-2-fluorophenylsulfonylaminomethyl)bicyclo[2.2.1]heptan-2-yl]-5Z-hexenoic acid

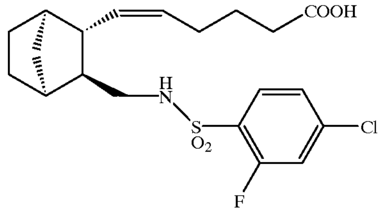

TLC: Rf 0.45 ($CHCl_3$:MeOH:$H_2O$=9:1:0.1);

NMR ($CDCl_3$): δ 7.89–7.81 (1H, m), 7.31–7.22 (2H, m), 5.33–5.14 (2H, m), 4.84 (1H, t-like), 3.12–2.83 (2H, m), 2.34 (2H, t, J=7.4 Hz), 2.19–1.09 (14H, m).

Example 5(e)

6-[(1R, 2S, 3S, 4S)-3-(4-chloro-2-methylphenylsulfonylaminomethyl)bicyclo[2.2.1]heptan-2-yl]-5Z-hexenoic acid

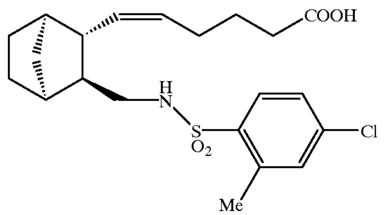

TLC: Rf 0.42 ($CHCl_3$:MeOH:$H_2O$=9:1:0.1);

NMR ($CDCl_3$): δ 7.90 (1H, d, J=9.0 Hz), 7.32–7.26 (2H, m), 5.35–5.14 (2H, m), 4.70 (1H, t-like), 3.07–2.75 (2H, m), 2.60 (3H, s), 2.34 (2H, t, J=7.4 Hz), 2.13–1.09 (14H, m).

Example 5(f)

6-[(1R, 2S, 3S, 4S)-3-(2,4,6-trichlorophenylsulfonylaminomethyl)bicyclo[2.2.1]-heptan-2-yl]-5Z-hexenoic acid

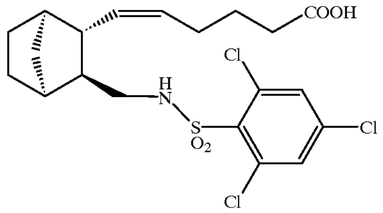

TLC: Rf 0.52 ($CHCl_3$:MeOH:$H_2O$=9:1:0.1);

NMR ($CDCl_3$): δ 7.49 (2H, s), 5.34–5.16 (3H, m), 3.18–2.85 (2H, m), 2.36 (2H, t, J=7.4 Hz), 2.18–1.09 (14H, m).

Example 5(g)

6-[(1R, 2S, 3S, 4S)-3-(4-chloro-2,6-dimethylphenylsulfonylaminomethyl)bicyclo[2.2.1]heptan-2-yl]-5Z-hexenoic acid

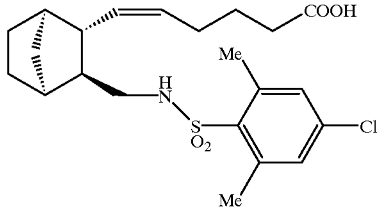

TLC: Rf 0.48 (AcOEt:hexane:AcOH=5:14:1);

NMR ($CDCl_3$): δ 7.16 (2H, s), 5.50–5.10 (2H, m), 4.57 (1H, brt, J=6.0 Hz), 3.10–2.90 (1H, m), 2.90–2.70 (1H, m), 2.65 (6H, s), 2.36 (2H, t, J=7.0 Hz), 2.20–2.00 (3H, m), 1.94–1.85 (1H, m), 1.85–1.40 (6H, m), 1.40–1.00 (4H, m).

Example 5(h)

6-[(1R, 2S, 3S, 4S)-3-(2,4-dichloro-6-methylphenylsulfonylaminomethyl)bicyclo[2.2.1]heptan-2-yl]-5Z-hexenoic acid

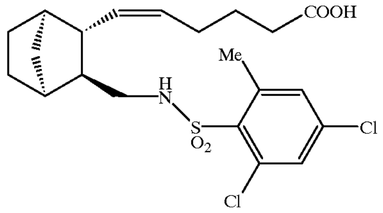

TLC: Rf 0.46 (AcOEt:hexane:AcOH=5:14:1);

NMR ($CDCl_3$): δ 7.41 (1H, d, J=1.5 Hz), 7.25 (1H, d, J=1.5 Hz), 5.40–5.10 (3H, m), 3.12–2.94 (1H, m), 2.90–2.74 (1H, m), 2.70 (3H, s), 2.35 (2H, t, J=7.5 Hz), 2.20 (1H, m), 2.15–2.00 (2H, m), 1.94–1.86 (1H, m), 1.82–1.40 (6H, m), 1.40–1.00 (4H, m).

Example 6(a)~6(h)

By the same procedure as Examples 1 and 2, the title compounds having the following physical data were obtained.

Example 6(a)

6-[(1S, 4R, 5S, 6S)-6-(2,4-dichlorophenylsulfonylaminomethyl)bicyclo[2.2.2]-oct-2-en-5-yl]-5Z-hexenoic acid

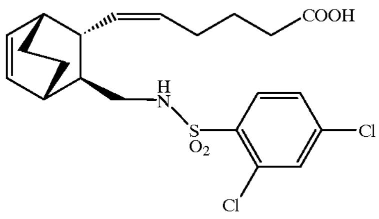

TLC: Rf 0.24 (hexane:AcOEt=1:1);

NMR ($CDCl_3$): $\delta$ 8.04 (1H, d, J=8.6 Hz), 7.55 (1H, d, J=1.6 Hz), 7.43 (1H, dd, J=8.6, 1.6 Hz), 6.32 (1H, t, J7.5 Hz), 6.16 (1H, t, J=7 Hz), 5.4–5.0 (3H, m), 3.0–2.8 (2H, m), 2.5–2.2 (3H, m), 2.2–2.0 (3H, m), 1.8–1.6 (2H, m), 1.5–1.0 (6H, m).

Example 6(b)

6-[(1S, 4R, 5S, 6S)-6-(2,4,6-trichlorophenylsulfonylaminomethyl)bicyclo[2.2.2]oct-2-en-5-yl]-5Z-hexenoic acid

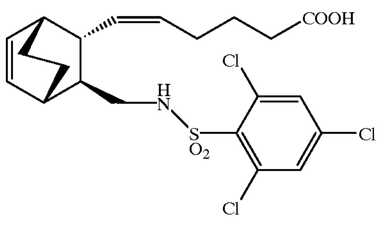

TLC: Rf 0.15 (hexane:AcOEt=1:1);

NMR ($CDCl_3$): $\delta$ 7.49 (2H, s), 6.3 (1H, m), 6.2 (1H, m), 5.4–5.0 (3H, m), 3.2–2.9 (1H, m), 2.4 (1H, m), 2.37 (2H, t, J=7.4 Hz), 2.3 (1H, m), 2.2–2.0 (4H, m), 1.8–1.0 (6H, m).

Example 6(c)

6-[(1S, 4R, 5S, 6S)-6-(4-chloro-2-methylphenylsulfonylaminomethyl)bicyclo-[2.2.2]oct-2-en-5-yl]-5Z-hexenoic acid

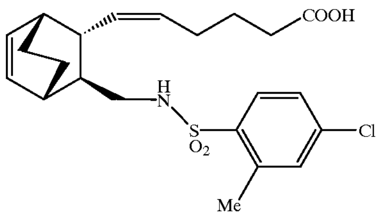

TLC: Rf 0.17 (hexane:AcOEt=1:1);

NMR ($CDCl_3$): $\delta$ 7.89 (1H, d, J=8 Hz), 7.3–7.2 (2H, m), 6.3 (1H, m), 6.15 (1H, t, J=7 Hz), 5.3–5.0 (2H, m), 4.7 (1H, m), 3.1–2.8 (2H, m), 2.61 (3H, s), 2.4 (1H, m), 2.37 (2H, t, J=7 Hz), 2.3 (1H, m), 2.2–2.0 (4H, m), 1.8–1.0 (6H, m).

Example 6(d)

6-[(1S, 4R, 5S, 6S)-6-(4-chloro-2-fluorophenylsulfonylaminomethyl)bicyclo[2.2.2]oct-2-en-5-yl]-5Z-hexenoic acid

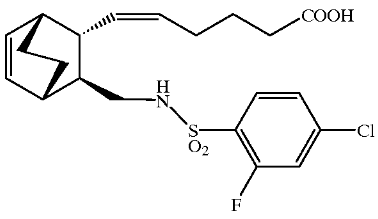

TLC: Rf 0.14 (hexane:AcOEt=1:1);

NMR ($CDCl_3$): $\delta$ 7.84 (1H, t, J=8 Hz), 7.3–7.2 (2H, m), 6.3 (1H, m), 6.16 (1H, t, J=7 Hz), 5.3–5.0 (2H, m), 4.9 (1H, m), 3.2–2.9 (1H, m), 2.4 (1H, m), 2.37 (2H, t, J=7.4 Hz), 2.3 (1H, m), 2.2–2.0 (4H, m), 1.8–1.0 (6H, m).

Example 6(e)

6-[(1S, 4R, 5S, 6S)-6-(4-chloro-2,6-dimethylphenylsulfonylaminomethyl)bicyclo[2.2.2]oct-2-en-5-yl]-5Z-hexenoic acid

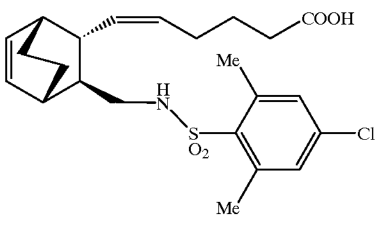

TLC: Rf 0.56 ($CHCl_3$:MeOH=9:1);

NMR ($CDCl_3$): $\delta$ 7.16 (2H, s), 6.30 (1H, dt, J=1.0, 7.2 Hz), 6.14 (1H, dt, J=1.0, 7.2 Hz), 5.3–5.0 (2H, m), 4.7–4.6 (1H, m), 3.1–2.9 (1H, m), 2.9–2.7 (1H, m), 2.64 (6H, s), 2.4–1.0 (14H, m).

Example 6(f)

6-[(1S, 4R, 5S, 6S)-6-(2,4-dichloro-6-methylphenylsulfonylaminomethyl)bicyclo[2.2.2]oct-2-en-5-yl]-5Z-hexenoic acid

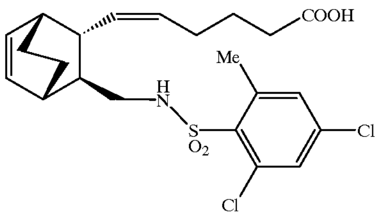

TLC: Rf 0.60 ($CHCl_3$:MeOH=9:1);

NMR ($CDCl_3$): $\delta$ 7.41 (1H, d, J=2.2 Hz), 7.25 (1H, d, J=2.2 Hz), 6.32 (1H, t, J=6.8 Hz), 6.16 (1H, t, J=6.8 Hz), 5.4–5.0 (3H, m), 3.1–2.9 (1H, m), 2.9–2.7 (1H, m), 2.70 (3H, s), 2.5–1.0 (14H, m).

Example 6(g)

6-[(1S, 4R, 5S, 6S)-6-(4-bromo-2-methylphenylsulfonylaminomethyl)bicyclo[2.2.2]oct-2-en-5-yl]-5Z-hexenoic acid

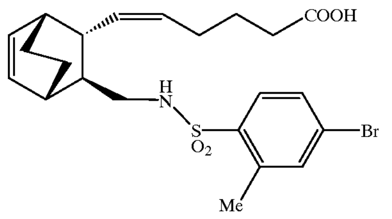

TLC: Rf 0.57 ($CHCl_3$:MeOH=9:1);

NMR ($CDCl_3$): δ 7.82 (1H, d, J=8.8 Hz), 7.5–7.4 (2H, m), 6.21 (1H, dt, J=1.0, 6.6 Hz), 6.15 (1H, t, J=6.6 Hz), 5.3–5.0 (2H, m), 4.70 (1H, t, J=6.0 Hz), 3.1–2.8 (2H, m), 2.60 (3H, s), 2.4–2.2 (4H, m), 2.2–1.9 (3H, m), 1.8–1.6 (2H, m), 1.6–1.0 (5H, m).

Example 6(h)

6-[(1S, 4R, 5S, 6S)-6-(2,4-dimethylphenylsulfonylaminomethyl)bicyclo[2.2.2]oct-2-en-5-yl]-5Z-hexenoic acid

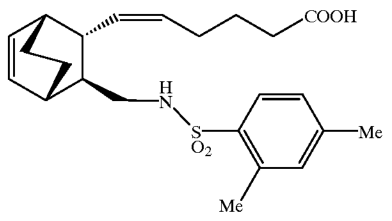

TLC: Rf 0.50 ($CHCl_3$:MeOH=9:1);

NMR ($CDCl_3$): δ 7.84 (1H, d, J=8.4 Hz), 7.2–7.1 (2H, m), 6.31 (1H, dt, J=1.0, 6.6 Hz), 6.14 (1H, t, J=6.6 Hz), 5.3–5.0 (2H, m), 4.57 (1H, t, J=6.0 Hz), 3.1–2.7 (2H, m), 2.58 (3H, s), 2.37 (3H, s), 2.4–1.9 (7H, m), 1.8–1.6 (2H, m), 1.5–0.9 (5H, m).

Example 7(a)~7(h)

By the same procedure as Examples 1 and 2, the title compounds having the following physical data were obtained.

Example 7(a)

6-[(1R, 4S, 5S, 6S)-6-(2,4-dichlorophenylsulfonylaminomethyl)bicyclo[2.2.2]-oct-2-en-5-yl]-5Z-hexenoic acid

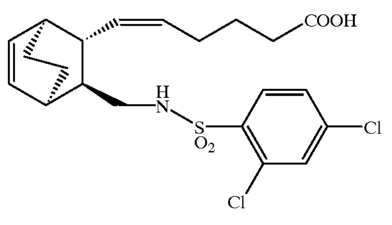

TLC: Rf 0.24 (hexane:AcOEt=1:1);

NMR ($CDCl_3$): δ 7.99 (1H, d, J=8.2 Hz), 7.54 (1H, d, J=2 Hz), 7.40 (1H, dd, J=8.6, 2 Hz), 6.37 (1H, t, J=7 Hz), 6.04 (1H, t, J=7 Hz), 5.4–5.3 (2H, m), 5.10 (1H, t, J=6 Hz), 2.61 (2H, t, J=6 Hz), 2.4 (1H, m), 2.36 (2H, t, J=7 Hz), 2.2 (1H, m), 2.1–2.0 (2H, m), 1.9 (1H, m), 1.8–1.7 (3H, m), 1.5–1.2 (3H, m), 1.2–1.0 (1H, m).

Example 7(b)

6-[(1R, 4S, 5S, 6S)-6-(4-chloro-2,6-dimethylphenylsulfonylaminomethyl)bicyclo[2.2.2]-oct-2-en-5-yl]-5Z-hexenoic acid

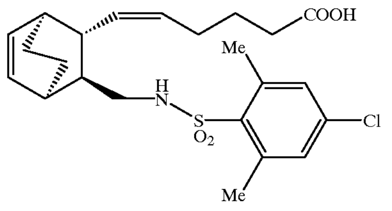

TLC: Rf 0.40 (AcOEt);

NMR ($CDCl_3$): δ 7.15 (2H, s), 6.36 (1H, m), 5.99 (1H, m), 5.48–5.28 (2H, m), 4.79 (1H, t, J=6 Hz), 2.68–2.57 (2H, m), 2.63 (6H, s), 2.41–2.00 (6H, m), 1.91–1.58 (4H, m), 1.50–0.92 (4H, m).

Example 7(c)

6-[(1R, 4S, 5S, 6S)-6-(2,4-dichloro-6-methylphenylsulfonylaminomethyl)bicyclo[2.2.2]oct-2-en-5-yl]-5Z-hexenoic acid

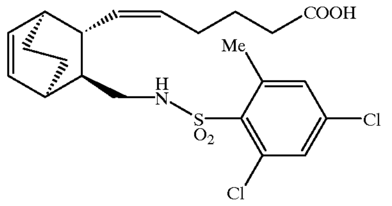

TLC: Rf 0.42 (AcOEt);

NMR ($CDCl_3$): δ 7.41 (1H, d, J=2 Hz), 7.23 (1H, d, J=2 Hz), 6.38 (1H, m), 6.06 (1H, m), 5.47–5.25 (3H, m), 2.72–2.20 (9H, m), 2.18–2.00 (2H, m), 1.94–1.60 (4H, m), 1.52–0.96 (4H, m).

Example 7(d)

6-[(1R, 4S, 5S, 6S)-6-(4-chloro-2-fluorophenylsulfonylaminomethyl)bicyclo[2.2.2]oct-2-en-5-yl]-5Z-hexenoic acid

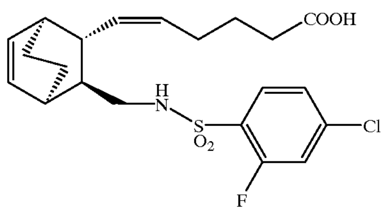

TLC: Rf 0.58 (AcOEt:hexane:AcOH=5:14:1);

NMR ($CDCl_3$): δ 7.81 (1H, t, J=7.5 Hz), 7.35–7.20 (2H, m), 6.37 (1H, t, J=7.0 Hz), 6.05 (1H, t, J=7.0 Hz), 5.60–5.25 (2H, m), 4.94 (1H, t, J=6.0 Hz), 2.82–2.50 (2H, m), 2.50–2.30 (1H, m), 2.37 (2H, t, J=7.5 Hz), 2.30–2.20 (1H, m), 2.20–1.95 (2H, m), 1.95–1.82 (1H, m), 1.82–1.60 (3H, m), 1.60–0.95 (4H, m).

Example 7(e)

6-[(1R, 4S, 5S, 6S)-6-(4-chloro-2-methylphenylsulfonylaminomethyl)bicyclo[2.2.2]oct-2-en-5-yl]-5Z-hexenoic acid

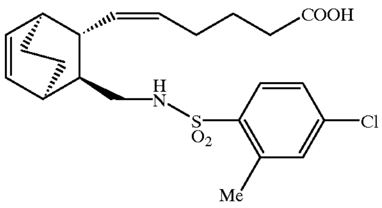

TLC: Rf 0.56 (AcOEt:hexane:AcOH=5:14:1);

NMR ($CDCl_3$): δ 7.86 (1H, d, J=8.0 Hz), 7.31 (1H, s), 7.28 (1H, d, J=8.0 Hz), 6.36 (1H, t, J=7.0 Hz), 5.99 (1H, t, J=7.0 Hz), 5.60–5.20 (2H, m), 4.84 (1H, t, J=6.0 Hz), 2.70–2.68 (2H, m), 2.60 (3H, s), 2.45–2.30 (1H, m), 2.37 (2H, t, J=7.0 Hz), 2.30–2.20 (1H, m), 2.20–2.00 (2H, m), 1.95–1.80 (1H, m), 1.80–1.60 (3H, m), 1.55–0.95 (4H, m).

Example 7(f)

6-[(1R, 4S, 5S, 6S)-6-(2,4,6-trichlorophenylsulfonylaminomethyl)bicyclo[2.2.2]oct-2-en-5-yl]-5Z-hexenoic acid

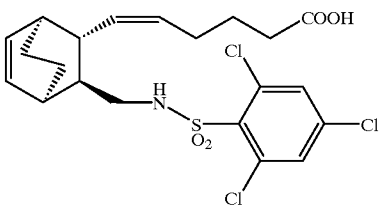

TLC: Rf 0.59 (AcOEt:hexane:AcOH=5:14:1);

NMR ($CDCl_3$): δ 7.48 (2H, s), 6.39 (1H, t, J=7.5 Hz), 6.08 (1H, t, J=7.5 Hz), 5.60–5.25 (3H, m), 2.72 (2H, t, J=6.5 Hz), 2.50–2.40 (1H, m), 2.37 (2H, t, J=7.5 Hz), 2.35–2.20 (1H, m), 2.20–2.10 (2H, m), 2.00–1.85 (1H, m), 1.80–1.60 (3H, m), 1.60–0.95 (4H, m).

Example 7(g)

6-[(1R, 4S, 5S, 6S)-6-(4-bromo-2-methylphenylsulfonylaminomethyl)bicyclo[2.2.2]oct-2-en-5-yl]-5Z-hexenoic acid

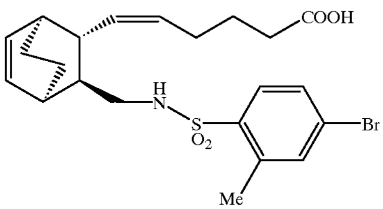

TLC: Rf 0.5 ($MeOH:CHCl_3$=1:9);

NMR ($CDCl_3$): δ 7.78 (1H, d, J=8.4 Hz), 7.5–7.4 (2H, m), 6.36 (1H, t, J=7.4 Hz), 6.00 (1H, t, J=7.4 Hz), 5.5–5.3 (2H, m), 4.85 (1H, t, J=6.0 Hz), 2.59 (3H, s), 2.7–2.5 (1H, m), 2.4–2.0 (6H, m), 1.9–1.6 (4H, m), 1.5–1.0 (5H, m).

Example 7(h)

6-[(1R, 4S, 5S, 6S)-6-(2,4-dimethylphenylsulfonylaminomethyl)bicyclo[2.2.2]oct-2-en-5-yl]-5Z-hexenoic acid

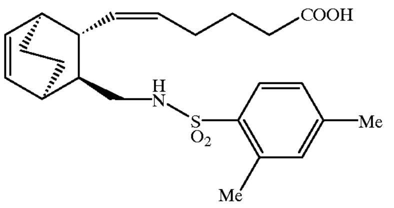

TLC: Rf 0.48 ($MeOH:CHCl_3$=1:9);

NMR ($CDCl_3$): δ 7.80 (1H, d, J=8.6 Hz), 7.2–7.0 (2H, m), 6.34 (1H, t, J=7.4 Hz), 5.98 (1H, t, J=7.4 Hz), 5.5–5.3 (2H, m), 4.72 (1H, t, J=6.2 Hz), 2.58 (3H, s), 2.7–2.5 (2H, m), 2.37 (3H, s), 2.4–2.0 (6H, m), 1.9–1.6 (4H, m), 1.5–1.2 (3H, m), 1.1–1.0 (1H, m).

Example 8(a)

By the same procedure as Examples 1 and 2, the title compound having the following physical data was obtained.

Example 8(a)

6-[(1R, 2S)-2-(2,4-dichlorophenylsulfonylaminomethyl)cycloheptyl]-5Z-hexenoic acid

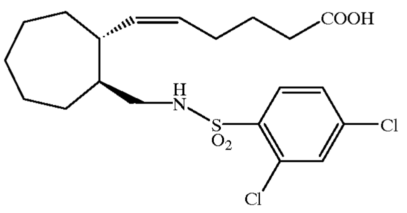

TLC: Rf 0.31 ($MeOH:CHCl_3$=1:10);

NMR ($CDCl_3$): δ 7.98 (1H, d, J=8 Hz), 7.53 (1H, d, J=2 Hz), 7.39 (1H, dd, J=8, 2 Hz), 5.37–5.17 (2H, m), 5.10 (1H, t, J=5 Hz), 2.82 (1H, m), 2.68 (1H, m), 2.33 (2H, t, J=7 Hz), 2.22–1.87 (3H, m), 1.87–1.10 (13H, m).

Reference Example 1

6-[(2S, 3S)-3-(t-butoxycarbonylaminomethyl)bicyclo[2.2.2]octan-2-yl]-5Z-hexenoic acid methyl ester

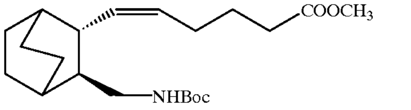

To a solution of 6-[(2S, 3S)-3-aminomethyl)bicyclo[2.2.2]octan-2-yl]- 5Z-hexenoic acid methyl ester (2.80 g) in methylene chloride (20 ml), triethylamine (1.8 ml) was added at 0° C. To this solution, a solution of di-t-butyl dicarbonate (2.92 ml) in methylene chloride (10 ml) was added dropwise. termination of reaction, the solution was quenched by adding water at 0° C. The reaction mixture was extracted with ethyl acetate. The organic layer was washed with water and saturated saline solution succeedingly, dried over anhydrous sodium sulfate, filtrated and concentrated under the reduced pressure to give the crude compound. This crude compound was purified with column chromatography (hexane-ethyl acetate) to give the title compound (3.10 g) having the following physical data as colorless oil.

TLC: Rf 0.44 (AcOEt:hexane=1:3);

NMR ($CDCl_3$): δ 5.50 (1H, dd, J=10, 10 Hz), 5.32 (1H, dt, J=10, 7 Hz), 4.57 (1H, brs), 3.67 (3H, s), 3.06 (2H, m), 2.32 (2H, t, J=7 Hz), 2.20–1.90 93H, m), 1.80–1.20 (22H, m).

Reference Example 2

6-[(2S, 3S)-3-(t-butoxycarbonylaminomethyl)bicyclo[2.2.2]octan-2-yl]-2E,5Z-hexadienoic acid methyl ester

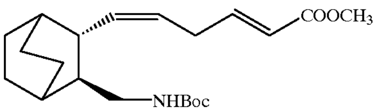

To a solution of lithium hexamethyldisilazido (1.0 M, 7 ml) in tetrahydrofuran (10 ml), a solution of the compound prepared in Reference Example 1 (1.02 g) in tetrahydrofuran (5 ml) was added dropwise at −78° C. The solution was stirred for 1 hour at −78° C. Succeedingly, a solution of diphenyl diselenide (1.92 g) in tetrahydrofuran (5 ml) was added dropwise thereto at −78° C. The solution was stirred for 20 minutes at −78° C., warmed to 0° C. and then stirred for 2 hours additionally. After the termination of reaction, water was added thereto at 0° C. The reaction mixture was extracted with ethyl acetate. The organic layer was washed with water and saturated saline solution succeedingly, dried over anhydrous sodium sulfate, filtrated and concentrated under the reduced pressure to give the crude compound. This crude compound was purified with column chromatography (hexane-ethyl acetate) to give the phenylselenyl compound (0.592 g) as bright yellow oil.

To a solution of this phenylselenyl compound (0.580 g) in mixture of tetrahydrofuran (6 ml) and ethyl acetate (12 ml), sodium hydrogen carbonate (0.196 g) was added. At 0° C., 30% $H_2O_2$ (0.250 ml) was added dropwise thereto. The solution was stirred for 1 hour at room temperature. The reaction mixture was poured into iced water and extracted with ethyl acetate. The organic layer was washed with water and saturated saline solution succeedingly, dried over anhydrous sodium sulfate, filtrated and concentrated under the reduced pressure to give the crude compound. This crude compound was purified with column chromatography (ethyl acetate-toluene) to give the title compound (0.259 g) having the following physical data as colorless viscous oil.

TLC: Rf 0.37 (AcOEt:toluene=1:10);

NMR ($CDCl_3$): δ 6.94 (1H, dt, J=15, 7 Hz), 5.84 (1H, dt, J=15, 1 Hz), 5.64 (1H, t, J=10 Hz), 5.37 (1H, dt, J=10, 7 Hz), 4.47 (1H, m), 3.72 (3H, s), 3.15–2.8 (4H, m), 2.10–1.90 (1H, m), 1.78–1.20 (20H, m).

Reference Example 3

6-[(2S, 3S)-3-aminomethylbicyclo[2.2.2]octan-2-yl]-2E,5Z-hexadienoic acid methyl ester·HCl salt

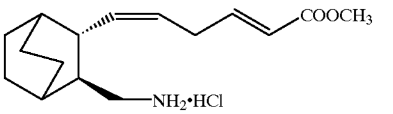

To a solution of the compound prepared in Reference Example 2 (0.245 g) in methanol (5 ml), 4N HCl-dioxane (2 ml) was added at 0° C. The solution was stirred for 12 hours. After the termination of reaction, the solution was concentrated under the reduced pressure to give the title compound (0.194 g) having the following physical data as white powder.

TLC: Rf 0.17 (MeOH:$CHCl_3$=1:5).

Example 9

6-[(2S, 3S)-3-(2,4-dichlorophenylsulfonylaminomethyl)bicyclo[2.2.2]octan-2-yl]-2E,5Z-hexadienoic acid methyl ester

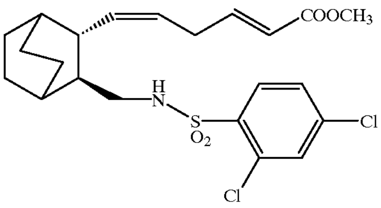

To a solution of a compound prepared in Reference Example 3 (0.194 g) in methylene chloride (10 ml), 2,4-dichlorobenzenesulfonylchloride (0.198 g) was added. The solution was cooled to 0° C. Triethylamine (0.226 ml) was added dropwise thereto. The solution was stirred for 1 hour at 0° C. After the termination of reaction, the solution was quenched by adding iced water, acidified by HCl and extracted with ethyl acetate. The organic layer was washed with water and saturated saline solution succeedingly, dried over anhydrous sodium sulfate, filtrated and concentrated under the reduced pressure to give the crude compound. This crude compound was purified with column chromatography (hexane-ethyl acetate) to give the title compound (0.285 g) having the following physical data as colorless viscous oil.

TLC: Rf 0.54 (AcOEt:hexane=1:2);

NMR ($CDCl_3$): δ 8.02 (1H, d, J=8 Hz), 7.55 (1H, s), 7.41 (1H, d, J=8 Hz), 6.92 (1H, dt, J=15, 7 Hz), 5.81 (1H, dd, J=15, 2 Hz), 5.54 (1H, dd, J=10, 10 Hz), 5.38 (1H, dt, J=10, 7 Hz), 4.89 (1H, t, J=5 Hz), 3.75 (3H, s), 3.00–2.70 (4H, m), 1.94 (1H, m), 1.80–1.20 (13H, m).

Example 10

6-[(2S, 3S)-3-(2,4-dichlorophenylsulfonylaminomethyl)bicyclo[2.2.2]octan-2-yl]-2E,5Z-hexadienoic acid

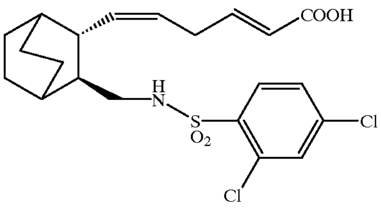

A compound prepared in Example 9 (0.267 g) was suspended with dimethylsulfoxide (25 ml) and buffer (pH 7.4, 50 ml). To this suspension, pig liver esterase (0.16 ml, 720 units) was added at 0° C. The suspension was stirred for 16 hours at room temperature. After then, to this suspension, pig liver esterase (0.16 ml, 720 units) was added at room temperature. The suspension was stirred for 16 hours at room temperature additionally. After the termination of reaction, the suspension was acidified by 1N HCl and extracted with ethyl acetate. The organic layer was washed with water and saturated saline solution succeedingly, dried over anhydrous sodium sulfate, filtrated and concentrated under the reduced pressure to give the crude compound. This crude compound was purified with column chromatography (methanol-chloroform) to give the title compound (0.114 g) having the following physical data as colorless viscous oil.

TLC: Rf 0.24 (MeOH:$CHCl_3$=1:10);

NMR ($CDCl_3$): δ 8.02 (1H, d, J=8 Hz), 7.54 (1H, d, J=2 Hz), 7.40 (1H, dd, J=8, 2 Hz), 7.00 (1H, dt, J=15. 7 Hz), 5.82 (1H, d, J=5 Hz), 5.57 (1H, t, J=10 Hz), 5.38 (1H, dt, J=10, 7 Hz), 4.93 (1H, t, J=5 Hz), 2.96 (2H, t, J=5 Hz), 2.82 (2H, m), 1.95 (1H, m), 1.74–1.20 (11H, m).

Formulation Example 1:

The following compounds were admixed in conventional method and punched out to obtain 100 tablets each containing 10 mg of active ingredient.

6-[(2s, 3s)-3-(2,4-dichlorophenylsulfonylaminomethyl)bicyclo[2.2.2]octan-2-yl]-5Z-hexenoic acid . . . 1.0 g cellulose calcium glycolate . . . 200 mg Magnesium stearate . . . 100 mg Micro crystalline cellulose . . . 9.7 g

What we claim is:

1. A benzenesulfonamide compound of the formula (I)

(I)

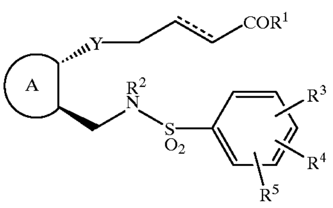

wherein, the formula

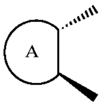

is the group of the formula (a)

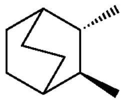
, (b)

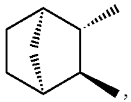
, (c)

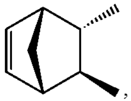
, (d)

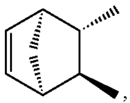
, (e)

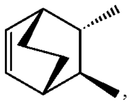
, (f)

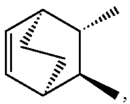
,

-continued (g)

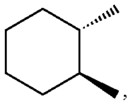
, (h)

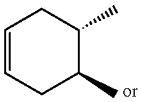
or (i)

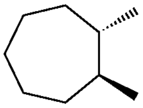

$R^1$ is hydroxy, C1~4 alkoxy or the group of the formula $NR^6R^7$ wherein, each $R^6$ and $R^7$ is, independently, hydrogen or C1~4 alkyl, $R^2$ is hydrogen or C1~4 alkyl, $R^3$ and $R^4$ are C1~4 alkyl, halogen or trifluoromethyl, $R^5$ is hydrogen, C1~4 alkyl, halogen or trifluoromethyl, Y is cis-vinylene or trans-vinylene, and the symbol

is single bond or double bond, non-toxic salt thereof or cyclodextrin clathrate thereof.

2. A compound according to claim 1, wherein the formula

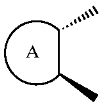

in the formula (I) is the group of the formula (a)

(a)

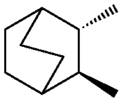
.

3. A compound according to claim 1 which is of the formula (I-1)

(I-1)

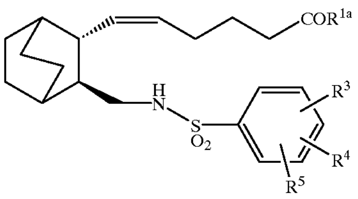

wherein, $R^{1a}$ is hydroxy or C1~4 alkoxy, and the other symbols are as defined in claim 1, non-toxic salt thereof or cyclodextrin clathrate thereof.

4. A compound according to claim 2, which is selected from the group consisting of 6-[3-(2,4-dichlorophenylsulfonylaminomethyl)bicyclo[2.2.2]octane-2-yl]-5Z-hexenoic acid, 6-[3-(2,4-dimethylphenylsulfonylaminomethyl)bicyclo[2.2.2]octane-2-yl]-5Z-hexenoic acid, 6-[3-(2,4-dibromophenylsulfonylaminomethyl)bicyclo[2.2.2]octane-2-yl]-5Z-hexenoic acid, 6-[3-(4-chloro-2-methylphenylsulfonylaminomethyl)bicyclo[2.2.2]octane-2-yl]-5Z-hexenoic acid, 6-[3-(4-bromo-2-methylphenylsulfonylaminomethyl)bicyclo[2.2.2]octane-2-yl]-5Z-hexenoic acid, 6-[3-(4-bromo-2-fluorophenylsulfonylaminomethyl)bicyclo[2.2.2]octane-2-yl]-5Z-hexenoic acid, 6-[3-(4-chloro-2-fluorophenylsulfonylaminomethyl)bicyclo[2.2.2]octane-2-yl]-5Z-hexenoic acid, 6-[3-(2,4-dichlorophenylsulfonylaminomethyl)bicyclo[2.2.2]octane-2-yl]-2E,5Z-hexenoic acid, 6-[3-(2,4,6-trichlorophenylsulfonylaminomethyl)bicyclo[2.2.2]octane-2-yl]-5Z-hexenoic acid, 6-[3-(2-chloro-4-methylphenylsulfonylaminomethyl)bicyclo[2.2.2]octane-2-yl]-5Z-hexenoic acid, 6-[3-(4-chloro-2-trifluoromethylphenylsulfonylaminomethyl)bicyclo[2.2.2]-octane-2-yl]-5Z-hexenoic acid, 6-[3-(2,4,6-trimethylphenylsulfonylaminomethyl)bicyclo[2.2.2]octane-2-yl]-5Z-hexenoic acid, 6-[3-(2,4-dichloro-6-methylphenylsulfonylaminomethyl)bicyclo[2.2.2]octane-2-yl]-5Z-hexenoic acid, 6-[3-(4-chloro-2,6-dimethylphenylsulfonylaminomethyl)bicyclo[2.2.2]octane-2-yl]-5Z-hexenoic acid, 6-[3-(2,4-dichlorophenylsulfonylaminomethyl)bicyclo[2.2.2]octan-2-yl]-5E-hexenoic acid and 6-[3-(4-chloro-2-methylphenylsulfonylaminomethyl)bicyclo[2.2.2]octan-2-yl]- 5E-hexenoic acid and methyl ester thereof.

5. A compound according to claim 1, wherein the formula

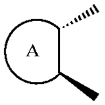

in the formula (I) is the group of the formula (b)

(b)

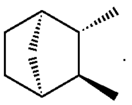

6. A compound according to claim 5, which is selected from the group consisting of 6-[3-(2,4-dichlorophenylsulfonylaminomethyl)bicyclo[2.2.1]heptan-2-yl]-5Z-hexenoic acid, 6-[3-(4-bromo-2-fluorophenylsulfonylaminomethyl)bicyclo[2.2.1]heptan-2-yl]-5Z-hexenoic acid, 6-[3-(4-bromo-2-methylphenylsulfonylaminomethyl)bicyclo[2.2.1]heptan-2-yl]-5Z-hexenoic acid, 6-[3-(4-chloro-2-fluorophenylsulfonylaminomethyl)bicyclo[2.2.1]heptan-2-yl]-5Z-hexenoic acid, 6-[3-(4-chloro-2-methylphenylsulfonylaminomethyl)bicyclo[2.2.1]heptan-2-yl]-5Z-hexenoic acid, 6-[3-(2,4,6-trichlorophenylsulfonylaminomethyl)bicyclo[2.2.1]heptan-2-yl]-5Z-hexenoic acid, 6-[3-(4-chloro-2,6-dimethylphenylsulfonylaminomethyl)bicyclo[2.2.1]heptan-2-yl]-5Z-hexenoic acid and 6-[3-(2,4-dichloro-6-methylphenylsulfonylaminomethyl)bicyclo[2.2.1]heptan-2-yl]-5Z-hexenoic acid and methyl ester thereof.

7. A compound according to claim 1, wherein the formula

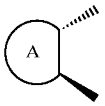

in the formula (I) is the group of the formula (c)

(c)

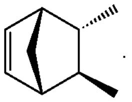

8. A compound according to claim 1, wherein the formula

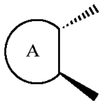

in the formula (I) is the group of the formula (d)

(d)

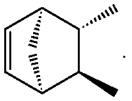

9. A compound according to claim 1, wherein the formula

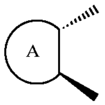

in the formula (I) is the group of the formula (e)

(e)

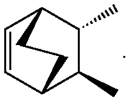

10. A compound according to claim 9, which is selected from the group consisting of 6-[6-(2,4-dichlorophenylsulfonylaminomethyl)bicyclo[2.2.2]oct-2-en-5-yl]-5Z-hexenoic acid, 6-[6-(2,4,6-trichlorophenylsulfonylaminomethyl)bicyclo[2.2.2]oct-2-en-5-yl]-5Z-hexenoic acid, 6-[6-(4-chloro-2-methylphenylsulfonylaminomethyl)bicyclo[2.2.2]oct-2-en-5-yl]-5Z-hexenoic acid, 6-[6-(4-chloro-2-fluorophenylsulfonylaminomethyl)bicyclo[2.2.2]oct-2-en-5-yl]-5Z-hexenoic acid, 6-[6-(4-chloro-2,6-dimethylphenylsulfonylaminomethyl)bicyclo[2.2.2]oct-2-en-5-yl]-5Z-hexenoic acid 6-[6-(2,4-dichloro-6-methylphenylsulfonylaminomethyl)bicyclo[2.2.2]oct-2-en-5-yl]-5Z-hexenoic acid, 6-[6-(4-bromo-2-methylphenylsulfonylaminomethyl)bicyclo[2.2.2]oct-2-en-5-yl]-5Z-hexenoic acid and 6-[6-(2,4-dimethylphenylsulfonylaminomethyl)bicyclo[2.2.2]oct-2-en-5-yl]-5Z-hexenoic acid and methyl ester thereof.

11. A compound according to claim 1, wherein the formula

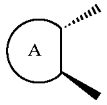

in the formula (I) is the group of the formula (f)

(f)

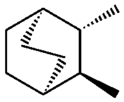

.

12. A compound according to claim 11, which is selected from the group consisting of 6-[6-(2,4-dichlorophenylsulfonylaminomethyl)bicyclo[2.2.2]oct-2-en-5-yl]-5Z-hexenoic acid, 6-[6-(4-chloro-2,6-dimethylphenylsulfonylaminomethyl)bicyclo[2.2.2]oct-2-en-5-yl]-5Z-hexenoic acid, 6-[6-(2,4-dichloro-6-methylphenylsulfonylaminomethyl)bicyclo[2.2.2]oct-2-en-5-yl]-5Z-hexenoic acid, 6-[6-(4-chloro-2-fluorophenylsulfonylaminomethyl)bicyclo[2.2.2]oct-2-en-5-yl]-5Z-hexenoic acid, 6-[6-(4-chloro-2-methylphenylsulfonylaminomethyl)bicyclo[2.2.2]oct-2-en-5-yl]-5Z-hexenoic acid, 6-[6-(2,4,6-trichlorophenylsulfonylaminomethyl)bicyclo[2.2.2]oct-2-en-5-yl]-5Z-hexenoic acid, 6-[6-(4-bromo-2-methylphenylsulfonylaminomethyl)bicyclo[2.2.2]oct-2-en-5-yl]-5Z-hexenoic acid and 6-[6-(2,4-dimethylphenylsulfonylaminomethyl)bicyclo[2.2.2]oct-2-en-5-yl]-5Z-hexenoic acid and methyl ester thereof.

13. A compound according to claim 1, wherein the formula

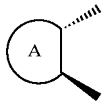

in the formula (I) is the group of the formula (g)

(g)

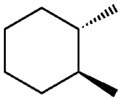

.

14. A compound according to claim 13, which is selected from the group consisting of 6-[2-(2,4-dichlorophenylsulfonylaminomethyl)cyclohexyl]-5Z-hexenoic acid, 6-[2-(4-bromo-2-fluorophenylsulfonylaminomethyl)cyclohexyl]-5Z-hexenoic acid, 6-[2-(4-bromo-2-methylphenylsulfonylaminomethyl)cyclohexyl]-5Z-hexenoic acid, 6-[2-(4-chloro-2-fluorophenylsulfonylaminomethyl)cyclohexyl]-5Z-hexenoic acid, 6-[2-(2,4,6-trichlorophenylsulfonylaminomethyl)cyclohexyl]-5Z-hexenoic acid, 6-[2-(4-chloro-2-methylphenylsulfonylaminomethyl)cyclohexyl]-5Z-hexenoic acid, 6-[2-(4-chloro-2,6-dimethylphenylsulfonylaminomethyl)cyclohexyl]-5Z-hexenoic acid and 6-[2-(2,4-dichloro-6-methylphenylsulfonylaminomethyl)cyclohexyl]-5Z-hexenoic acid and methyl ester thereof.

15. A compound according to claim 1, wherein the formula

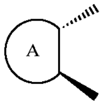

in the formula (I) is the group of the formula (h)

(h)

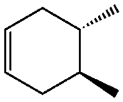

.

16. A compound according to claim 15, which is selected from the group consisting of 6-[5-(2,4-dichlorophenylsulfonylaminomethyl)cyclohexen-4-yl]-5Z-hexenoic acid, 6-[5-(4-chloro-2-methylphenylsulfonylaminomethyl)cyclohexen-4-yl]-5Z-hexenoic acid, 6-[5-(4-chloro-2-fluorophenylsulfonylaminomethyl)cyclohexen-4-yl]-5Z-hexenoic acid, 6-[5-(4-bromo-2-fluorophenylsulfonylaminomethyl)cyclohexen-4-yl]-5Z-hexenoic acid, 6-[5-(2,4,6-trichlorophenylsulfonylaminomethyl)cyclohexen-4-yl]-5Z-hexenoic acid, 6-[5-(4-bromo-2-methylphenylsulfonylaminomethyl)cyclohexen-4-yl]-5Z-hexenoic acid, 6-[5-(2,4-dichloro-6-methylphenylsulfonylaminomethyl)cyclohexen-4-yl]-5Z-hexenoic acid and 6-[5-(4-chloro-2,6-dimethylphenylsulfonylaminomethyl)cyclohexen-4-yl]-5Z-hexenoic acid and methyl ester thereof.

17. A compound according to claim 1, wherein the formula

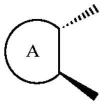

in the formula (I) is the group of the formula (I)

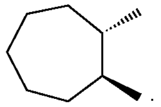

(i)

18. A compound according to claim 17, which is selected from the group consisting of 6-[2-(2,4-dichlorophenylsulfonylaminomethyl)cycloheptyl]-5Z-hexenoic acid and methyl ester thereof.

19. An antagonist of EP1 receptor which is a prostaglandin $E_2$ receptor subtype comprising a benzenesulfonamide compound of the formula (I) depicted in claim 1, non-toxic salt thereof or cyclodextrin clathrate thereof as an active ingredient.

20. A method for the treatment of pain, fever or pollakiuria which comprises administering an effective amount of a benzenesulfonamide compound of the formula (I) depicted in claim 1, non-toxic salt thereof or cyclodextrin clathrate thereof with a pharmaceutically carrier or coating.

* * * * *